(12) United States Patent
Kuret et al.

(10) Patent No.: US 7,172,875 B2
(45) Date of Patent: Feb. 6, 2007

(54) IDENTIFYING INHIBITORS OF INTRACELLULAR PROTEIN FIBRILLIZATION

(75) Inventors: Jeff Kuret, Dublin, OH (US); Carmen N. Chirita, Dublin, OH (US); Mihaela Necula, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/783,795

(22) Filed: Feb. 18, 2004

(65) Prior Publication Data

US 2005/0153384 A1    Jul. 14, 2005

Related U.S. Application Data

(60) Provisional application No. 60/536,324, filed on Jan. 13, 2004, provisional application No. 60/448,034, filed on Feb. 18, 2003.

(51) Int. Cl.
*G01N 33/53* (2006.01)
(52) U.S. Cl. ...................................... 435/7.1
(58) Field of Classification Search ................. 435/7.1
See application file for complete search history.

(56) References Cited

U.S. PATENT DOCUMENTS

| | | | |
|---|---|---|---|
| 6,177,472 B1 * | 1/2001 | Wilson et al. | 514/646 |
| 6,458,847 B1 * | 10/2002 | Wilson et al. | 514/646 |
| 6,479,528 B1 | 11/2002 | Kuret et al. | |
| 2002/0151464 A1 | 10/2002 | Wolozin et al. | |
| 2002/0152480 A1 | 10/2002 | Biere et al. | |
| 2002/0164657 A1 | 11/2002 | Sharma et al. | |
| 2002/0168687 A1 | 11/2002 | Wischik et al. | |
| 2002/0197737 A1 | 12/2002 | Mandelkow et al. | |

OTHER PUBLICATIONS

Cohlberg et al., "Heparin and Other Glycosaminoglycans Stimulate the Formation of Amyloid Fibrils from alpha-Synuclein in Vitro". Biochemistry. 2002. vol. 41, pp. 1502-1511.*
Definition of Surfactant from Wikipedia: (http://en.wikipedia.org. wiki.Surfactant), 2005.*
International search report for PCT application No. PCT/US2004/005097.
King, et al., Differential Assembly of Human Tau Insoforms in the Presence of Arachidonic Acid J. Neurochem., 74, 1749-1757, 2000.
Tabaton, et al, Ultrastructural localization of beta-amyloid, tau and ubiquitin eptiopes in extracellular neurfibrillary, Proc Nat Acad Sci, vol. 88, p. 2098-2102, Mar. 1991.
Lansbury, Jr., Fibrillogenesis and Neurodegenerative Diseases. What is the Link?, Natl. Acad. Sci. USA vol. 96, pp. 3342-3344, Mar. 1999.
Pompe-Novak, et al., Neural inclusions in the light of new findings on protein fibrillization, Cognitive Neuroscience, Information Society 2001, pp. 72-75.
Caughey, et al., Protofibrils, Pores, Fibrils, and Neurodegeneration: Separating the Responsible Protein Aggregates from the Innocent Bystanders, Annu. Rv. Neurosci. 2003.
Necula, et al., Rapid anionic Micelle-mediated Synuclein Fibrillization in Vitro, The Journal of Biological Chemistry, vol. 278, Nov. 21, pp. 46674-46680, 2003.
Chirita, et al., Anionic Micelles and Vesicles Induce Tau Fibrillization in Vitro, The Journal of Biological Chemistry, vol. 278, No. 28, Jul. 11, pp. 25644-25650, 2003.
Alonso, et al., Hyperphosphorylation indcues self-assembly of into tangles of paired helical filaments/straight filaments, PNAS, vol. 98, No. 12, Jun. 5, 2001, pp. 6923-6928.
Sontag, et al., Molecular Interactions Among Protein Phosphatase 2A, Tau, and Microtubules, Journal of Biological Chem., vol. 274, No. 36, pp. 25490-25498, Sep. 3, 1999.
Crystal, et al., A comparison of amyloid fibrillogenesis using the novel fluorescent compound K114, Journal of Neurochemistry, 86, pp. 1359-1368, 2003.
Forman, et al., Convergence of Tau and Synuclein Pathology in Neurodegenerative Disease, American Society for Investigative Pathology, 2003.
Rochet, et al., Inhibition of fibrillization and accumulation of prefibrillar oligomers in mixtures of human and mouse alpha-synuclein, Biochem., 39(35):10619-26, Sep. 5, 2000.
Chitra, et al., Ligand-Dependent Inhibition and Reversal of Tau Filament, Biochemistry 2004, 43, 2879-2887.
Necula, et al., Electron microscopy as a quantative method for investigating tau fibrillization, Analytical Biochemistry 329 (2004) 238-246.
Necula, et al., A static laser light scattering assay for surfactant-induced tau fibrillization, Analytical Biochemistry 333 (2004) 205-215.

(Continued)

*Primary Examiner*—Jon Weber
*Assistant Examiner*—Suzanne M. Noakes
(74) *Attorney, Agent, or Firm*—Calfee, Halter & Griswold LLP

(57) ABSTRACT

Methods for identifying and characterizing inhibitors of protein filament formation are provided. These methods are particularly useful for identifying those agents which inhibit or prevent protein filament formation within neurons of mammalian subjects, particularly human subjects, such as the formation of tau filaments in Alzheimer's patients, and α-synuclein filaments in Parkinson's patients. According to the methods, protein monomers which are associated with formation of intra- or extra-cellular aggregates are combined under physiological conditions with a fibrillization inducer and the formation of protein aggregates is assessed in the absence and the presence of a test agent. The absence or a reduction in the size or stability of proteinaceous polymeric filaments as compared to a control indicates that the test agent is an inhibitor of proteinaceous polymeric filament formation.

28 Claims, 12 Drawing Sheets

OTHER PUBLICATIONS

Necula, et al., Pseudophosphorylation and Glycation of Tau Protein Ehnance but Do Not Trigger Fibrillization in Vitro, The Journal of Biological Chemistry, vol. 279, No. 48, Nov. 26, pp. 49694-49703, 2004.

Necula, et al., Site-specific pseudophosphorylation modulates the rate of tau filament dissociation, FEBS Letters 579 (2005) 1435-1457.

Kuret, et al., Pathways of tau fibrillization, Biochimica et Biophysica Acta 1739 (2005) 167-178.

Guibin, et al., Casein Kinase 1 Delta Phosphorylates Tau and Disrupts Its Binding to Microtubules, The Journal of Biochemical Chemistry, vol. 279, No. 16, Apr. 16, pp. 15938-15945, 2004.

Chirita et al. Triggers of Full-Length Tau Aggregation: A Role for Partially Folded Intermediates, Biochemistry 44 5862-5872 2005.

Chirita, et al., Evidence for an Intermediate in Tau Filament Formation, Biochemistry 43, 1704-1714 2004.

\* cited by examiner

IDENTIFYING INHIBITORS OF INTRACELLULAR PROTEIN FIBRILLIZATION

CROSS REFERENCE TO RELATED APPLICATIONS

This application claims priority to U.S. Provisional Applications No. 60/536,324, filed Jan. 13, 2004, and No. 60/448,034, filed Feb. 18, 2003, each of which is incorporated herein by reference in its entirety.

GOVERNMENT RIGHTS

This invention was supported, at least in part, by NIH grant AG14452. The Federal Government has certain rights in this invention.

TECHNICAL FIELD OF THE INVENTION

The current invention relates to tools for screening and identifying agents that inhibit or prevent protein filament formation. Such tools are particularly useful for identifying those agents which inhibit or prevent protein filament formation within neurons of mammalian subjects, particularly human subjects, such as the formation of tau filaments in Alzheimer's patients, and α-synuclein filaments in Parkinson's patients.

BACKGROUND

A variety of diseases are characterized by the intracellular accumulation of proteinaceous filaments. Abnormal protein aggregation in the form of fibrillar protein deposits ("fibrillization"), or amyloid plaques, characterizes many if not all neurodegenerative disorders, as well as degenerative diseases that affect the pancreas, heart, kidneys, and other tissues. For example, filaments comprised of the microtubule-associated protein tau accumulate within the neurons of patients afflicted with Alzheimer's disease, and filaments of α-synuclein form within affected neurons of basal ganglia in Parkinson's patients. Aggregation of the microtubule-associated protein tau into filamentous lesions is a hallmark pathology of Alzheimer's Disease ("AD") and other tauopathic neurodegenerative diseases. There is increasing evidence that abnormal protein aggregation, both intra and extracellular, is a cause, rather than merely an effect, of these degenerative diseases. A great deal of circumstantial evidence has been reported in the scientific literature that suggests this causal influence. Genetic studies have linked genes encoding aggregated proteins to familial forms of a variety of diseases; animal modeling studies have shown that overexpression of aggregated proteins leads to disease associate phenotypes; and biophysical studies have shown that disease associated mutations to the genes encoding aggregated proteins promote protein aggregation in vitro.

Based on the evidence that abnormal formation of protein filaments influences the development of a variety of diseases, it would be desirable to design therapeutic strategies for interfering with the fibrillization process. One such therapeutic strategy is the targeted use of inhibitors of fibrillization. Identification and evaluation of the function of such inhibitors would be facilitated by an in vitro system in which filament formation can be reliably produced, controlled and observed. Optimally, such as system would permit the identification and evaluation of ihibitors of the discrete step or steps in the fibrillization process.

In vitro studies with one aggregating protein involved in AD, tau, have shown that fibrillization of full-length, unphosphorylated recombinant tau can be induced under near physiological conditions by treatment with either fatty acids, or the polyanionic substances RNA, and sulfated glycosaminoglycans, including heparin, dextran sulfate, and pentosan polysulfate. However, the time-frames for achieving fibrillization vary widely among these various inducers. For example, the timeframes for achieving fibrillization with polyanionic substances can be on the order of days, and are thus impractical for most high-throughput screening uses. Likewise, use of fatty acids such as arachadonic acid ("AA") has disadvantages. The susceptibility of unsaturated fatty acids such as AA to oxidation, influences their activity and eventually renders them inert.

Accordingly, it would be desirable to have in vitro methods and model systems for identifying and evaluating potential inhibitors of protein fibrillization under physiologic conditions that are free of the limitations of existing methods. Such methods and model systems would not rely on labile reagents, and would be suitable for conducting rapid and high throughput in vitro screening assays of fibrillization inhibitors. Inhibitors identified using such methods and model systems would be useful for the treatment or prevention of disorders involving intracellular fibrillization, such as Alzheimer's and Parkinson's Diseases.

SUMMARY OF THE INVENTION

In one embodiment, the present invention provides screening methods for identifying inhibitors of protein filament formation, comprising:

a) providing:
  i) a protein monomer associated with formation of intra- or extra-cellular aggregates;
  ii) a fibrillization inducer selected from the group consisting of anionic microparticles, anionic support surfaces, and anionic surfactants having an alkyl chain comprising at least 12 carbon atoms and an anionic head group; and
  iii) a test compound;
b) combining said protein monomer and said fibrillization inducer in one or more control reaction vessels;
c) combining said protein monomer, said fibrillization inducer, and said test compound in one or more test reaction vessels; and
d) analyzing the contents of the control reaction vessels of step (b) and the test reaction vessels of step (c) for the formation of proteinaceous polymeric filaments, wherein absence or a reduction in the size or stability of proteinaceous polymeric filaments in the test reaction vessels of step (c) as compared to proteinaceous polymeric filaments in the control reaction vessels of step (b) indicates that the test compound is an inhibitor of proteinaceous polymeric filament formation.

In one aspect, the protein monomer is selected from the group consisting of tau monomer and α-synuclein monomer. Preferably, the protein monomer is provided at a concentration of 0.1 to 70 μM. More preferably, the concentration of the protein monomer is from 0.1–10 μM and most preferably the concentration is from 0.1–5 μM. In one preferred embodiment, the protein monomer is provided at a concentration of 4 μM. In another preferred embodiment, the protein monomer is provided at a concentration of 0.5 μM.

The fibrillization inducer may be an anionic microparticle, such as a microsphere, having an overall negative charge with a molecular area from 12–62 Å$^2$/eq, such as a carboxylate conjugated polystyrene microsphere. The anionic microparticles are preferably provided in the size range of 40–90 nm diameter, preferably at a concentration from 1 to 800 µM, and more preferably at a concentration of from 50 to 300 µM.

The fibrillization inducer may be an anionic support surface, such as a glass slide or plate, a plastic plate or tray, or other inert support surface which has an anionic surface charge character. The total charge density of the anionic support surface may be determined and optimized to control the amount of intermediate formed and also to limit the number of fibrillization nucleation sites.

The fibrillization inducer may be an anionic surfactant having an alkyl chain comprising at least 12 carbon atoms and an anionic head group. Suitable anionic surfactants may be selected from the group consisting of sulfate, carboxylate detergents, sulfonate detergents, and phosphate detergents. Examples of acceptable anionic surfactants include non-esterified carboxylate detergents, non-esterified phosphono carboxylate detergents, non-esterified sulfo carboxyate detergents, alkyl sulfate detergents, alkyl polyol sulfate detergents, alkyl thiosulfate detergents, alkyl oxypropyl sulfate detergents, alkyl oxyethylene sulfate detergents, alkyl sulfonate detergents, hydroxy alkyl sulfonate detergents, alkaryl sulfonate detergents, and para alkaryl sulfonate detergents. The anionic surfactant has an alkyl chain that is either saturated or unsaturated. In another aspect, the anionic surfactant is an anionic phospholipid. Examples of suitable anionic phospholipids include but are not limited to phosphatidylserine and phosphatidic acid. The surfactant is preferably provided at a concentration from 50 to 150 µM. More preferably, the concentration is from 50 to 100 µM.

The monomer, fibrillization inducer, and test compound may be combined either simultaneously or sequentially.

Formation of filaments may be analyzed by a variety of methods known in the art, such as electron microscopy, fluorescence spectroscopy, ultracentrifugation, and light scattering.

In another embodiment, the present invention provides methods for identifying drugs useful in the treatment of Alzheimer's Disease. Such methods comprise contacting tau protein monomer with a tau fibrillization inducer selected from the group consisting of anionic microparticles, anionic support surfaces, and anionic surfactants having an alkyl chain comprising at least 12 carbon atoms and an anionic head group, and a test compound, and determining whether the test compound inhibits tau fibrillization. Preferably, the tau protein monomer is provided at a concentration of 1 to 70 µM. More preferably, the concentration of the tau protein monomer is from 1–10 µM and most preferably the concentration is from 3–5 µM. In one preferred embodiment, the tau protein monomer is provided at a concentration of 1 to 70 µM, and the tau fibrillization inducer is an anionic microsphere having a molecular area from 12–62 Å$^2$/eq. In a particularly preferred embodiment the tau protein monomer is provided at a concentration of from 1–10 µM and the fibrillization inducer is an anionic microsphere having a diameter of 90 nm and a molecular area of 12 Å$^2$/eq. In another preferred embodiment, the tau fibrillization inducer is an anionic surfactant provided at a concentration from 50 to 150 µM, and selected from the group consisting of sulfate, carboxylate detergents, sulfonate detergents, and phosphate detergents. In a particularly preferred embodiment, the tau protein monomer is provided at a concentration of 4 µM, and the tau fibrillization inducer has the chemical formula $C_{18}H_{37}SO_4Na$.

In another embodiment, the present invention provides methods for identifying drugs useful in the treatment of Parkinson's disease. Such methods comprise: contacting α-synuclein monomer with a α-synuclein fibrillization inducer selected from the group consisting of anionic microparticles, anionic support surfaces, and anionic surfactants having an alkyl chain comprising at least 12 carbon atoms and an anionic head group, and a test compound, and determining whether the test compound inhibits α-synuclein fibrillization. Preferably, the α-synuclein protein monomer is provided at a concentration of 1 to 70 µM. More preferably, the concentration of the α-synuclein protein monomer is from 1–10 µM and most preferably the concentration is from 3–5 µM. In one preferred embodiment, the α-synuclein protein monomer is provided at a concentration of 1 to 70 µM, and the α-synuclein fibrillization inducer is an anionic microsphere having a molecular area from 12–62 Å$^2$/eq. In a particularly preferred embodiment the α-synuclein protein monomer is provided at a concentration of from 1–10 µM and the fibrillization inducer is an anionic microsphere having a diameter of 90 nm and a molecular area of 12 Å$^2$/eq. In another preferred embodiment, the α-synuclein fibrillization inducer is an anionic surfactant provided at a concentration from 50 to 150 µM, and selected from the group consisting of sulfate, carboxylate detergents, sulfonate detergents, and phosphate detergents. In a particularly preferred embodiment, the α-synuclein protein monomer is provided at a concentration of 4 µM, and the α-synuclein fibrillization inducer has the chemical formula chemical formula $C_{12}H_{25}SO_4Na$.

In another embodiment, the present invention provides model systems for identifying inhibitors of tau protein fibrillization, comprising tau monomer and a fibrillization inducer selected from the group consisting of anionic microparticles, anionic support surfaces, and micellar anionic surfactants having an alkyl chain comprising at least 12 carbon atoms and an anionic head group, wherein the tau monomer and the fibrillization inducer interact to induce the formation of tau filaments.

In another embodiment, the present invention provides model systems for identifying inhibitors of α-synuclein protein fibrillization, comprising α-synuclein monomer and a fibrillization inducer selected from the group consisting of anionic microparticles, anionic support surfaces, and micellar anionic surfactants having an alkyl chain comprising at least 12 carbon atoms and an anionic head group, wherein the α-synuclein monomer and the fibrillization inducer interact to induce the formation of α-synuclein filaments.

In another embodiment, the present invention provides methods for identifying drugs which prevent or inhibit the formation of intra-neuronal tau filaments that are associated with Alzheimer's Disease in a human subject in need of the same, according to the methods previously described, wherein the protein monomer is a tau monomer.

In another embodiment, the present invention provides methods for identifying drugs which prevent or inhibit the formation of intra-neuronal α-synuclein filaments that are associated with Parkinson's Disease in a human subject in need of the same, according to the methods previously described, wherein the protein monomer is α-synuclein.

BRIEF DESCRIPTION OF THE DRAWINGS

The present invention may be more readily understood by reference to the following drawings wherein.

DETAILED DESCRIPTION OF THE INVENTION

Figure 1:
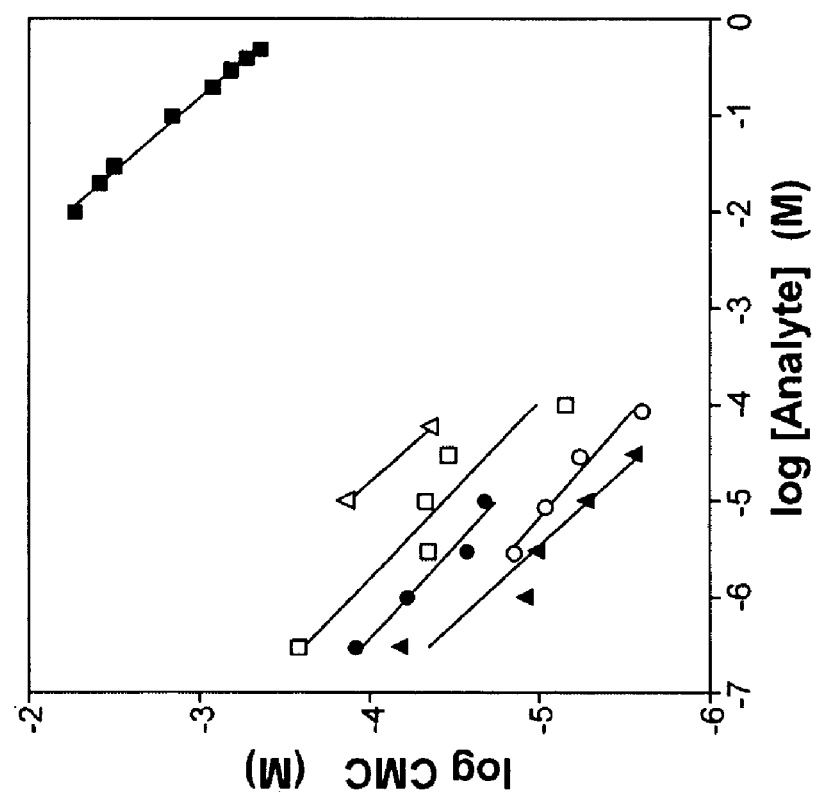
FIG. 1 shows Corrin-Harkins Analysis of Analyte-mediated CMC Depression. CMC values for SDS were determined in the presence α-synuclein (□; 0.3, 3, 10, 30, 100 μM), htau40 (●; 0.3, 1, 3, 10 μM), protamine (○; 3, 10, 30, 100 μM), and histone (▲; 0.3, 1, 3, 10, 30 μM), and plotted against protein concentration on double-logarithmic axes. Literature values for NaCl (■) and uteroglobin[4-14] (△) were plotted as well for comparison (28, 29). Each line represents the least squares fit of each data set to the empirical Corrin-Harkins equation (21) described in Experimental Procedures (eq 1). The data show that regardless of net charge, proteins are powerful depressors of detergent CMC, and far more potent than simple salts such as NaCl.

"Anionic bodies" as used herein means negatively charged particles such as anionic microspheres, and micellar structures comprised of anionic surfactants. In one aspect, anionic bodies are described herein as components of swellings that are observed, using electron microscopy, associated at one end with forming and elongating protein filaments. Anionic bodies serve as nucleation surfaces and induce fibrillization of protein monomers, such as tau and α-synuclein monomers.

"Anionic support surfaces" as used herein refers to a substrate or solid support comprised of a material that is modified to present a negative charge on its surface and that is generally flat, planar, convex or concave, such as reaction vessel walls, plates, slides and the like.

"Fibrillization inducer" as used herein means negatively-charged structures which induce and stabilize the nucleation and elongation of proteinaceous filaments. Examples of fibrillization inducers include anionic bodies, such as anionic micelles comprised of surfactants having an alkyl chain comprising at least 12 carbon atoms and an anionic head group and anionic microparticles, and anionic support surfaces.

"Micelle" as used herein means a submicroscopic aggregation of molecules which have a hydrophilic charged moiety attached to an elongated portion that is essentially hydrophobic, an example of such molecules being an anionic surfactant comprising at least 12 carbon atoms and an anionic head group, wherein the submicroscopic aggregation is globular, and wherein the hydrophobic portions of the molecules are oriented toward the center of the globule and the hydrophilic charged moieties are oriented such that the interior of the globule is essentially nonpolar and the surface of the globule has an overall negative charge.

"Micellar anionic surfactants" refers to anionic surfactants having an alkyl chain comprising at least 12 carbon atoms and an anionic head group which are organized into micelles in the presence of protein monomers that are capable of fibrillization.

Methods and Tools for Screening for Inhibitors of Fibrillization

According to the present invention, the methods and tools described herein can be used to screen for inhibitors of fibrillization. Such inhibitors are candidates for prophylactic and therapeutic agents for treating mammalian subjects, particularly human subjects, who have developed, or are at risk for developing disorders associated with intracellular fibrillization of proteins. Inhibitors of tau fibrillization are useful, for example, for the treatment of Alzheimer's Disease. Inhibitors of α-synuclein are useful, for example, for the treatment of Parkinson's Disease.

Protein Monomers Useful for Inhibitor Screening

Protein monomers useful according to the methods of the present invention include any of a variety of protein monomers which are involved in filament formation in a variety of cellular pathologies, particularly neurological pathologies. Examples of such proteins include tau protein, which is involved in proteinaceous inclusions in Alzheimer's Disease, and α-synuclein, which is involved in the formation of inclusions in Parkinson's disease. Protein monomers may be obtained through various commercial sources, or may alternatively be prepared using protein isolation from biological samples or produced using a recombinant expression system. Other proteins that form abnormal intra- or extra-cellular aggregates in a variety of degenerative diseases include, but are not limited to: islet amyloid polypeptide and β-amyloid protein, which are a natively unfolded protein like tau and α-synuclein; huntingtin; transthyretin; acyl phosphotase; lysozyme; acylphosphatase; cystatin C; prion protein; crystallins; ataxins; cathepsin B; and other fibrilizing proteins also known in the art to be associated with pathologies.

Protein monomers are used at physiological concentrations. Preferably, the protein monomer is provided at a concentration of 0.1 to 70 μM. More preferably, the concentration of the protein monomer is from 0.1–10 μM and most preferably the concentration is from 0.1–5 μM. In one preferred embodiment, the protein monomer is provided at a concentration of 4 μM. In another preferred embodiment, the protein monomer is provided at a concentration of 0.5 μM.

Surfactants as Fibrillization Inducers that are Useful for Inhibitor Screening

The fibrillization inducer may be an anionic surfactant selected from the group consisting of sulfate, carboxylate detergents, sulfonate detergents, and phosphate detergents.

"Surfactant" (surface active agent) means a substance which lowers the surface tension of the medium in which it is dissolved, and/or the interfacial tension with other phases, and, accordingly, is positively adsorbed at the liquid/vapour and/or at other interfaces. 1972, 31, 611, IUPAC Compendium of Chemical Terminology 2nd Edition (1997). "Detergent" means a surfactant (or a mixture containing one or more surfactants) having cleaning properties in dilute solution (soaps are surfactants and detergents). 1972, 31, 612, IUPAC Compendium of Chemical Terminology 2nd Edition (1997).

Examples of acceptable anionic surfactants inculdes non-esterified carboxylate detergents, non-esterified phosphono carboxylate detergents, non-esterified sulfo carboxyate detergents, alkyl sulfate detergents, alkyl polyol sulfate detergents, alkyl thiosulfate detergents, alkyl oxypropyl sulfate detergents, alkyl oxyethylene sulfate detergents, alkyl sulfonate detergents, hydroxy alkyl sulfonate detergents, alkaryl sulfonate detergents, and para alkaryl sulfonate detergents. The anionic surfactant has an alkyl chain that is either saturated or unsaturated. In another aspect, the anionic surfactant is an anionic phospholipid. Examples of anionic phospholipids include phosphatidylserine and phosphatidic acid.

The surfactant is preferably provided at a concentration from 50 to 150 µM, and more preferably at a concentration from 50 to 100 µM.

Microparticles and Microspheres as Fibrillization Inducers that are Useful for Inhibitor Screening As used herein, "anionic microparticles" means particles which have negatively charged surfaces. Microparticles may be irregular in shape, in which case under microscopic examination they have a shape that is not a substantially sphere or spheroidal (ellipsis). Microspheres have, under microscopic examination, substantially a sphere or a spheroidal shape (ellipsis). A sphere is defined as a volume that presents the lowest external surface area. In one aspect, the surface of microspheres appear smooth under less than 1000-fold magnifications. The shape of irregular particles is often the result of a larger solid particle that has been crushed. In contrast to microspheres, each irregular particle appears non-uniform in shape as compared to microspheres. Also in contrast to microspheres, irregular particles have rough surface. The length, thickness and depth of irregular particles are not uniform; they show angles and protuberances on the surface. These particles also appear irregular in their ability to transmit light under microscopic examination, depending on the thickness of the particles at particular locations.

Suitable microparticle compositions include, but are not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. Microparticles may be made from organic polymers, such as polyacrylates, acrylamide/sodium acrylate (AcAm/NaAc) copolymers, polyacrylamidopropylaulfonic acid (poly AMPS), acrylamide/acrylamidopropylsulfonic acid (AcAm/AMPS) copolymers and terpolmers containing acrylamide/sodium acrylate/acrylamidopropylsulfonic acid (AcAm/NaAc/AMPS). Alternatively, microparticles may be made from a colloidal inorganic material, such as colloidal silica (varying particle sizes), colloidal zinc or aluminum, colloidal borosilicate, various clays (betonites, hectorites, smectites), colloidal aluminas and zincs and alum. "Microsphere Detection Guide" from Bangs Laboratories, Fishers Ind. is a helpful guide to the identification and selection of microparticles.

Microparticle sizes are provided in the nanometer range, i.e. 50 nm, with microparticles from about 10 nm to about 100 nm being preferred, and from about 40 to about 90 nm being particularly preferred, although in some embodiments smaller or larger microparticles may be used.

Anionic microparticles preferably have a molecular area from 12–62 Å$^2$/eq. In one embodiment, the diameter of the microparticle is 90 nm and the molecular area is 12 Å$^2$/eq. The anionic microparticles are preferably provided at a concentration from 1 to 800 pM, more preferably at a concentration of from 50 to 300 pM.

The surfaces of anionic microparticles are comprised of linked, negatively charged moieties such as carboxyl and carboxylate, sulfate and phosphate.

Anionic microparticles, such as anionic microspheres, offer a convenient alternative for studying surface-mediated protein aggregation in vitro. They can be obtained with defined surface chemistry in uniform sizes that, unlike surfactant micelles, do not change with concentration or ionic strength. In contrast to mica slabs, their small diffusion boundary layer makes them especially suitable for kinetic studies. Moreover, they can facilitate observation of individual nucleation and extension events by electron microscopy owing to their easily identifiable profile. Because of their tight association with filaments, microspheres can provide an internal standard for quantitation of fibrillization, so that in future it may be possible to normalize single electron micrographs to the entire reaction volume, and therefore calibrate such data in terms of molar concentration.

Support Surfaces as Fibrillization Inducers that are Useful for Inhibitor Screening By "substrate" or "solid support" or other grammatical equivalents herein is meant any material that can be modified to present a negative surface charge. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce. Surface modification of substrates is achieved using techniques known in the art whereby a variety of differently negatively charged chemical moieties are bound to the surface of the substrate. Many surface modified anionic substrates are available commercially.

Generally the substrate is flat (planar), although as will be appreciated by those in the art, other configurations of substrates may be used as well; for example, three dimensional configurations can be used, for example the substrate may be the inside surface of a tube, for flow-through sample analysis to minimize sample volume. Other examples include flat planar substrates such as glass, polystyrene and other plastics and acrylics.

Screening for Inhibitors of Fibrillization

According to one embodiment, inhibitors of protein filament formation may be identified using the following screening method. A protein monomer, a fibrillization inducer selected from the group consisting of anionic microparticles, anionic support surfaces, and anionic surfactants having an alkyl chain comprising at least 12 carbon atoms and an anionic head group; and a test compound are provided. In one or more control reaction mixtures, the protein monomer and fibrillization inducer are combined, and optionally, in parallel, in one or more test reaction mixtures, the protein monomer and fibrillization inducer are combined. The contents of the reaction mixtures are analyzed for the formation of proteinaceous polymeric filaments. The absence or a reduction in the size or stability of proteinaceous polymeric filaments in the test reaction mixtures as compared to proteinaceous polymeric filaments in the control reaction mixtures indicates that the test compound is an inhibitor of proteinaceous polymeric filament formation.

According to this embodiment, the protein monomer is provided at a concentration of 0.1 to 70 µM. More preferably, the concentration of the protein monomer is from 0.1–10 µM and most preferably the concentration is from 0.1–5 µM.

Also according to this embodiment, the selected fibrillization inducer is provided at the following concentration:

Anionic microparticles preferably have a molecular area from 12–62 Å$^2$/eq. In one embodiment, the diameter of the microparticle is 90 nm and the molecular area is 12 Å$^2$/eq. The anionic microparticles are preferably provided at a concentration from 1 to 800 µM, more preferably at a concentration of from 50 to 300 µM.

Anionic support surfaces have a total charge density that is optimized to control the amount of intermediate formed and also to limit the number of fibrillization nucleation sites.

Anionic surfactants are preferably provided at a concentration from 50 to 150 µM, and more preferably at a concentration from 50 to 100 µM.

Formation of filaments may be analyzed by a variety of methods known in the art, such as electron microscopy, fluorescence spectroscopy, ultracentrifugation, and light scattering.

Assays for Screening Inhibitors of Protein Intermediates Involved in Fibrillization According to another embodiment, inhibitors of protein filament formation may be identified using the general screening method previously described to specifically screen for inhibitors of fibrillization that interact with protein intermediates involved in the fibrillization pathway. According to such methods, the protein monomer is provided at a concentration of 0.1–5 µM, and more preferably at a concentration of 0.5 µM.

Examples of suitable methods for analyzing the assays according to this embodiment include electron microscopy, fluorescence spectroscopy, ultracentrifugation, and light scattering; particularly suitable are fluorescence spectroscopy and light scattering.

Assays for Screening Inhibitors of Protein Filament Nucleation, Elongation or Stability According to yet another embodiment, inhibitors of protein filament formation may be identified using the general screening method previously described to specifically screen for inhibitors of fibrillization that influence filament nucleation, elongation, or stability. According to such methods, the protein monomer is provided at a concentration of the concentration range from 2 µM to 70 µM, more preferably from 2 µM to 10 µM, and most preferably from 2 µM to 5 µM.

Examples of suitable methods for analyzing the assays according to this embodiment include electron microscopy, fluorescence spectroscopy, ultracentrifugation, and light scattering; particularly suitable are electron microscopy and, ultracentrifugation.

Unless otherwise defined herein, all technical and scientific terms used herein have the same meaning as commonly understood by one of ordinary skill in the art to which this invention pertains. Although methods and materials similar or equivalent to those described herein can be used to practice the invention, examples of suitable methods and materials are described below. All publications, patent applications, patents, and other references mentioned herein are incorporated herein by reference, in their entirety. In case of conflict between the present specification and any publications, patent applications, patents, and other references mentioned herein, the present specification, including the definitions provided herein, will control. In addition, the materials, methods, and examples are illustrative only and are not limiting.

Other features and advantages of the invention will be apparent from the following drawings, detailed description and examples, and from the claims.

Description of the Mechanism of Anionic Surface-Mediated Fibrillization

The aforementioned tools and methods of the present disclosure are provided based on Applicants discovery and first reported description of the sequence of mechanistic events that accompany microsphere- and surfactant-induced tau and α-synuclein fibrillization. An aspect of Applicants discoveries is the identification of the involvement of a partially folded intermediate in the formation of filaments. Based on these discoveries, has described tools and methods for identifying agents that disrupt or inhibit formation of protein filaments, such as the tau and α-synuclein filaments that are observed in cells of patients with Alzheimer's and Parkinson's diseases. Applicant further provides herein a detailed summary of the mechanism of anionic-surface induced fibrillization, and examples demonstrating the use of these tools and methods.

Because the maturation of amorphous aggregates into neurofibrillary tangles correlates with cognitive impairment, clarifying the mechanistic pathway through which these changes occur is of critical importance. Filaments isolated from end-stage AD are well characterized, and consist of all six full-length tau isoforms that are extensively phosphorylated and organized into twisted PHFs and non-twisted SFs. Although tau filaments isolated from post mortem tissue display disease dependent gross morphology and tau isoform composition, they are thought to share the cross-beta sheet conformation typical of "amyloid". As a result, they bind anionic dyes such as thioflavin S and thiazin red. But the folding pathway though which tau protein, which when isolated in solution exists as a natively unfolded monomer, assembles into filaments has been described only on the macroscopic level. Among the earliest changes observable in AD-derived tissue specimens is the formation of non-fibrillar cytoplasmic aggregates of hyperphosporylated tau. These amorphous aggregates, as well as the earliest detectable fibrillar tau aggregates, frequently appear associated with membranous intracellular structures, suggesting that membranes may participate in the tau folding pathway.

In living cells and brain tissue, tau protein has been estimated as comprising 0.025–0.25% of total protein. Assuming intracellular protein concentrations of ~200 mg/ml yields estimates of total intracellular tau levels of 1–10 µM. At these concentrations, purified recombinant tau isoforms do not detectably aggregate over days of incubation under physiological conditions. However, aggregation and fibrillization of tau protein can be greatly accelerated under near physiological conditions in vitro by the addition of a variety of agents. These agents, which are powerful inducers of beta-sheet structure in many proteins, abruptly form micelles above a critical concentration in aqueous solution.

Applicant reports here for the first time that induction of fibrillization with anionic surfaces proceeds by the following pathway. Using tau as an example of a protein monomer and anionic surfactant such as an alkyl sulfate as an example of an anionic surface, the first step involves binding of surfactant in dispersed form to natively unfolded tau protein. As with other polyelectrolytes, the initial interactions are likely electrostatic and result in accumulation of surfactant at sites along the tau molecule, eventually leading to cooperative and localized surfactant aggregation well below the critical micellar concentration (CMC) observed in the absence protein. The dependence of CMC depression on tau concentration, as revealed by Corrin-Harkins plots, suggests that while cationic interactions certainly influence micelle stabilization, hydrophobic interactions may also play a role. It has been shown that the combination of these interactions can not only reduce CMC, but also effectively anchor polymers to individual micelles. A homogeneous solution of surfactant-bound tau protein is unlikely to result from these interactions. Rather, because micellization is highly cooperative and the number of interacting sites on tau is limited, tau protein is predicted to adopt a bimodal distribution consisting of surfactant bound and unbound populations. Computational models and direct laboratory evidence for such distributions have been reported in other systems. The proportion of tau that is surfactant bound is predicted to increase as surfactant concentrations rise, until at saturation equilibrium shifts completely toward the micelle-bound state. As a result, lower quantities of unfolded tau are available to support intermolecular reactions such as filament nucleation and extension, giving rise to the biphasic surfactant dose response curve as competing intramolecular reactions (such as α-helix formation) predominate.

The association of surfactant micelles with tau protein initiates conformation changes that culminate in fibrillization and formation of cross beta sheet structure. It has been argued that binding of surfactant in dispersed form is responsible for inducing beta sheet structure in many proteins of diverse primary structure including β2-glycoprotein I and complement receptor 1 derived peptide. But these studies did not appreciate the ability of protein to greatly lower surfactant CMC, and at least in the case of both tau and α-synuclein fibrillization, inducing activity actually resides with the micelle rather than dispersed surfactant. Results presented here show that conformational changes accompanying formation of the tau/surfactant mixed micelle do not necessarily form a template for addition of tau monomer. Rather, it is the creation of negatively charged micellar surface that plays the key role in the process. In fact, results with anionic microspheres suggest that no interaction between tau and inducer is necessary beyond simple adsorption, since these impermeable bodies promote fibrillization much like surfactants with respect to kinetics and biphasic potency. Consistent with this model, preformed lipid vesicles also nucleate tau filament formation.

The second step in the pathway appears to involve binding of the free tau population to the anionic surface, which leads to rapid formation of a ThS-positive intermediate without a lag period. The potency of anionic surfaces with respect to the initial rate of intermediate formation and the maximal extent of ThS fluorescence change is directly proportional to the concentration of negative charges. The ThS sensitive intermediate is metastable; it relies on the presence of anionic surface for its existence. When surfactant is withdrawn, the intermediate rapidly disappears, suggesting it is not fibrillar (synthetic filaments are stable for at least 90 min after withdrawal of surfactant). Rather, ThS reactivity suggests that it represents a beta structure-containing species which can serve as a nucleation site in the folding pathway leading to fibrils. The intermediate does not appear to represent dimer, because dimerization alone does not yield ThS fluoresence. Micelle-tau interactions stabilize not only the intermediate, but the entire micelle as well. As a result, micelles that normally have average lifetimes shorter than 1 s survive for hours as tau-decorated structures, becoming visible in the electron microscope as small particles at early time points and swellings at the end of growing filaments later in the time course.

The final step in the pathway involves fibrillization. It follows classic nucleation-dependent kinetics, consisting of a nucleation phase characterized by a pronounced lag time, followed by an exponential growth phase characterized by an apparent first order growth rate, $k_{app}$, and then an equilibrium phase where further filament growth ceased. Typically, only one filament >50 nm in length matures per microsphere, although morphological evidence suggested that multiple nucleation events are possible. Assuming similar behavior for anionic surfactant micelles explains the differing length distributions and concentration dependencies measured for htau40 and AA, $C_{18}H_{37}NaSO_4$, and $C_{20}H_{41}NaSO_4$. The number of filaments reflects the number of nucleation centers, which is proportional to the micelle concentration and thus dependent on the interplay between CMC and aggregation number:

$$m=(S_T-CMC)/N_a$$

where m is micelle concentration, $S_T$ is total surfactant concentration, and $N_a$ is the aggregation number. Up to the peak of its biphasic dose response curve, increasing micelle concentrations yield more nucleation centers and therefore more filaments that, at constant tau concentration, achieve shorter average lengths. Comparison among tau isoforms is more complicated, as these differ in the concentration dependence of nucleation as reflected in lag time.

Once nucleated, tau filaments grow unidirectionally from the inducer surface. The presence of only one actively growing end distinguishes the pathway described here from spontaneous aggregation pathways followed by other amyloids. At equilibrium, tau filaments remain associated with nucleation centers, explaining the substoichiometric recovery of AA with filaments. Previously, this observation was ascribed to transient association, but the work presented herein suggests it derives from unidirectional elongation combined with stable association. The final length distribution of the filament population is exponential owing to the time dependent nucleation event, as opposed to filament breakage or equilibrium considerations. Authentic, AD-derived filaments also show exponential length distributions, suggesting that time-dependent nucleation events such as those described here may play a role in their formation. However, purified filaments represent only a portion of total filaments in AD lesions, and also the susceptibility of isolated filaments to shearing and breakage has been noted previously. Thus, estimates of the length distribution and number average length of authentic filaments must be interpreted with caution.

Certain members of the Congo red family of dyes inhibit the fibrillization of several proteins, including tau. The model presented here suggests the prefibrillar intermediate may be the binding target for some members of this class of inhibitors. The intermediate binds ThS with micromolar affinity, suggesting it contains at least partially folded structure in beta sheet conformation. Although ThS itself is not inhibitory at 10 µM concentration (data not shown), other ligands may interact with the dye binding site so as to trap the intermediate and inhibit its participation in subsequent nucleation events. Trapping of the intermediate could also raise the apparent minimal concentration of tau necessary to support filaments at equilibrium, potentially leading to disassembly of mature filaments before they become irreversibly crosslinked. Thus unlike the natively unfolded tau monomer, the partially folded intermediate may represent a tractable target for inhibitor design. The model predicts that inhibitory selectivity among amyloids may be achievable on the basis of assembly mechanism.

EXAMPLES

The invention may be better understood by reference to the following examples, which serve to illustrate but not to limit the present invention.

Example 1

Assays for Tau Fibrillization

Materials. Recombinant His-tagged htau40 was prepared as described previously. AD-derived PHFs prepared as in were generously supplied by Dr. Lester I. Binder (Northwestern University Medical School, Chicago, Ill.). Arachidonic acid (AA) was obtained from Cayman Chemicals (Ann Arbor, Mich.), and stored at −80° C. under argon until used. Alkyl sulfate detergents (12, 18, and 20 carbons) were obtained from Mallinckrodt (Paris, Ky.), Lancaster Synthesis (Pelham, N.H.), and Research Plus (Bayonne, N.J.), respectively, as sodium salts. Glutaraldehyde, uranyl acetate, and 300 mesh carbon-coated copper grids were from Electron Microscopy Sciences (Ft. Washington, Pa.). N-Phenyl-1-naphthylamine, ThS, Protamine (grade IV from salmon) and histone (type II-A from calf thymus) were from Sigma (St. Louis, Mo.). Stocks of protamine and histone were made in water at 800 µM and used the same day. Carboxylate conjugated polystyrene microspheres of defined nominal diameter and molecular area (a measure of surface charge density reported in units of Å$^2$/eq) were obtained from Bangs Laboratories, Inc (Fishers, Ind.). Cationic colloidal gold (20 nm gold particles conjugated to poly-Lys) was from Ted Pella (Redding, Calif.).

Aggregation assays. Under standard conditions, htau40 (4 µM) was incubated without agitation in Assembly Buffer (10 mM HEPES, pH 7.4, 100 mM NaCl, 5 mM dithiothreitol) at 37° C. for up to 168 h in the presence or absence of fibrillization inducer (AA, alkyl sulfate detergents, or carboxylate modified polystyrene beads). All samples incubated for more than 24 h were kept under argon in parafilm-sealed tubes. Samples were processed for assay by electron microscopy as described below.

Electron Microscopy Assays. Aliquots of tau polymerization reactions were treated with 2% glutaraldehyde (final concentration), mounted on formvar/carbon-coated 300 mesh grids, and negatively stained with 2% uranyl acetate as described previously. Random images were viewed in a Phillips CM 12 transmission electron microscope operated at 65 kV, captured on film at 8,000–100,000-fold magnification, digitized at 600 dots-per-inch resolution, and imported into Optimas 6.5.1 for quantification of filament lengths and numbers. Individual filaments (defined as any object greater than 50 nm in its long axis with both ends visible in the field of view) were counted manually.

For colloidal gold labeling experiments, sample aliquots were processed as described above except that they were treated (1 h at 37° C.) with cationic gold (diluted 1:100 from stock in Assembly Buffer without DTT) in a humid chamber prior to uranyl acetate staining.

For freeze fracture analysis, aliquots of the polymerization reactions were quickly frozen onto gold "hats" in liquid ethane cooled by liquid nitrogen, and then loaded into a pre-cooled Balzer Freeze Etching System (BAF 400T; Balzer Corp., Hudson, N.H.). Frozen samples were fractured at −120° C. under vacuum (9×10$^{-7}$ mbar) and shadowed with platinum at an angle of 45° and with carbon perpendicular to the samples. Samples were rotated as the carbon evaporated to yield a more even coating, then removed from the instrument and thawed. Replicas were floated off the samples into distilled water, then transferred to Clorox bleach and digested for 1 h. Replicas were subsequently rinsed several times with distilled water and were further digested in two changes of methanol, followed by 30 min in methanol:chloroform (13:87). Replicas were then placed on 300 mesh copper grids and visualized as above.

Thioflavin S Fluorescence Measurements. Tau (4 µM) was aggregated at 37° C. as described above except that the reactions contained 10 µM ThS. Resultant changes in fluorescence were monitored at $\lambda_{ex}$=440 nm and $\lambda_{em}$=495 nm in a FlexStation plate reader (Molecular Devices, Sunnyvale, Calif.) operated at sensitivity 10, high PMT using black-matrix, clear-bottom 96-well isoplates (Wallac, Turku, Finland) sealed with transparent foil (NUNC; Denmark). Readings were made every 15 min after initiating reactions by addition of inducer and were corrected using protein-free control reactions.

For disaggregation studies, purified htau40 (4 µM) was preaggregated (3 h at room temperature) with AA (75 µM) as described above, then diluted 20-fold into Assembly Buffer containing ThS (2 µM) and either 4 µM htau40, 50 µM arachidonic acid, or no additions. ThS fluorescence was then followed over time with constant stirring.

Example 2

CMC Measurements.

CMC values for SDS were estimated at 37° C. using N-phenyl-1-naphthylamine as described previously, except that various concentrations of protamine, histone, α-synuclein, or htau40 were included with the samples. Detergent stock solutions were prepared in 1:1 water isopropanol.

Analytical Methods. Dependence of detergent CMC on protein concentration was fit to the empirical Corrin-Harkins equation:

$$\log \text{CMC} = -k_{CH}(\log n) + b_{CH} \quad (1)$$

where n is the molar concentration of protein or salt and $k_{CH}$ and $b_{CH}$ are constants. The slope of these curves, $k_{CH}$, approximates the proportion of detergent micelles that are ionized.

Sigmoidal reaction progress curves were fit to the sigmoidal logistic equation:

$$y = y_0 + \frac{A}{(1 + e^{-k_{app}(t-t_{50})})} \quad (2)$$

where y is total filament length (50 nm cutoff) measured at time t, $y_o$ is total filament length at time zero, $t_{50}$ is time to 50% maximum fibrillization, A is the maximum total filament length at equilibrium, and $k_{app}$ is the apparent first order rate constant for fibril growth in units of $time^{-1}$. Lag times, defined as the time where the tangent to the point of maximum polymerization rate intersects the abscissa of the sigmoidal curve were calculated as $t_{50}-(2/k_{app})$.

Hyperbolic reaction progress and concentration dependence curves were fit to the rectangular hyperbola:

$$y = \frac{ax}{b+x} \quad (3)$$

where y is fluorescence or initial velocity determined at time or concentration x, and constant b corresponds to x at 50% $y_{max}$ (i.e., $t_{50}$ or 50% maximum rate).

Initial rates were calculated from hyperbolic reaction progress curves by fitting the data to the polynomial series:

$$y=\alpha+\beta t+\gamma t^2+\ldots+\zeta t^6 \quad (4)$$

where y is fluorescence intensity at time t, and the coefficient β approximates the initial rate.

Equivalents of microsphere surface charge were calculated from the equation:

$$eq/bead=(\pi \cdot d^2 \cdot 10^2)/A \quad (5)$$

where d is bead diameter in nm, and A is molecular area in $Å^2$/eq.

Filament length distributions were fit to the exponential equation:

$$y=\alpha e^{bx} \quad (6)$$

where y is the percentage of all filaments filling a bin of length interval x, and b is a constant reported in units of $length^{-1}$±95% confidence interval.

Statistics. The proportions of filaments associated endwise with beads, and of beads associated with filaments, was estimated using the Wilson score method and reported ±95% confidence limit.

CMC Depression is Protein Concentration Dependent. Surfactant micelle stability reflects the balance between forces that promote (e.g., the hydrophobic effect mediated by alkyl chains) and oppose (e.g., electrostatic repulsion mediated by ionic headgroups) micellization. Thus, micelle stability, as reflected in CMC values, is sensitive to additives that modulate these interactions such as simple salts and proteins. To quantify the effect of tau on anionic micelle stability, the dependence of CMC depression on tau molar concentration was determined and compared to literature values for NaCl. The analysis also included α-synuclein, a protein with net negative charge at assay pH previously shown to depresses CMC, literature values for uteroglobulin[4-14], a hydrophobic undecapeptide of neutral net charge, and histone and protamine, two extremely basic proteins rich in clustered positive charge. The concentration dependence of CMC depression was linear for all experiments when plotted on double log axes (FIG. 1), consistent with the empirical Corrin-Harkins treatment of counterion effects on CMC (eq 1; Ref. 21). The slopes of these plots, which approximate both the proportion of micelle ionization and the degree of counterion binding, were similar (average slope=0.59±0.08; n=6), indicating there was little selectivity among protein counterions, regardless of isoelectric point or net charge. Significant differences in concentration dependence were apparent, however, with proteins being 5–7 orders of magnitude more potent than the simple salt NaCl on a molar basis. Only a portion of this difference could be ascribed to polyvalency, as the neutral peptide uteroglobulin[4-14], with its two positive charges, was still 1000-fold more potent than NaCl. Normalizing concentrations for either net or mol % positive charge tightened the potency distribution, but proteins were still at least 4 orders of magnitude more potent than NaCl. These data suggest that hydrophobic interactions between polypeptide and detergent make an important contribution to CMC depression, and that as a result even amphoteric proteins with net negative charges such as α-synuclein strongly depress detergent CMC at low micromolar concentrations.

Example 3

Micelles Serve as Nucleation Centers for Tau Fibrillization: Identification of Anionic Bodies on Protein Filaments.

Figure 2:
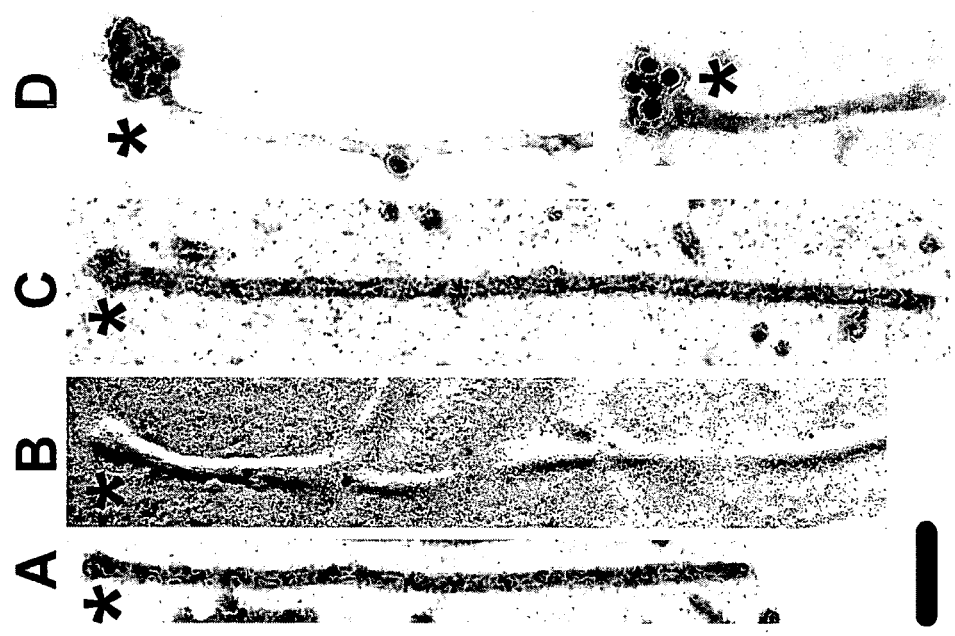
FIG. 2 provides data showing that Anionic Surfactants Induce Unidirectional tau Filament Growth. Htau40 (4 μM) was incubated (37° C.) in the presence of 50–100 μM A, AA; B, $C_{18}H_{37}NaSO_4$; or C, D, $C_{20}H_{41}NaSO_4$ and then examined by negative stain (A, C, D) or freeze fracture (B) transmission electron microscopy. In all cases, tau filaments were found extending from swellings located primarily at one filament end (asterisks). D, swellings were selectively labeled with 20-nm cationic gold particles, suggesting they contain concentrated anionic charge. Bar=50 nm.

When tau is incubated with preassembled anionic phospholipid vesicles, fibrillization proceeds from the vesicle surface, suggesting a key role for such surfaces in filament nucleation. However, it has been shown that when oppositely charged protein/surfactant pairs are coassembled, hierarchical structures more complicated than simple micelles or vesicles can form. To clarify the structural relationship between surfactant and tau in coassembly reactions, tau was fibrillized in the presence of AA and alkyl sulfate detergents ($C_{18}H_{37}NaSO_4$ and $C_{20}H_{41}NaSO_4$) and viewed by electron microscopy. These inducers were chosen because their long alkyl chains yield the largest micelles of any surfactants known to fibrillize tau in vitro. Low concentrations (<50 μM) of these agents yielded filaments with only a slight swelling seen at few filament ends (data not shown). But micelle size is dependent on total surfactant concentration, and above 50 μM these swellings became obvious for AA (FIG. 2A), $C_{18}H_{37}NaSO_4$ (FIG. 2B) and $C_{20}H_{41}NaSO_4$ (FIG. 2C). Typically, swellings were seen at only one end of a filament (FIGS. 2A, C, D). They were not an artifact of negative staining, because they also could be seen in preparations analyzed by freeze fracture methods (FIG. 2B). The swellings could correspond to detergent micelles, as predicted by the morphology of lipid vesicle-induced tau filaments, or to protein aggregates, as predicted by the micellar model of β-amyloid aggregation. To distinguish these possibilities, $C_{20}H_{41}NaSO_4$-induced tau filaments were stained with cationic colloidal 20-nm gold particles, which preferentially bind negatively charged surfaces such as those presented by anionic micelles. Resultant transmission electron micrographs showed intense staining of swellings, suggesting that they marked the location of detergent micelles that were preferentially localized at one end of each filament (FIG. 2D). These morphological findings are consistent with detergent aggregates formed in the presence of tau protein having energies of formation nearly identical to authentic micelles formed in buffer alone, and suggest that simple micelles are sufficient to induce tau fibrillization. Furthermore, these data suggest that micelles serve to nucleate tau fibrillization with subsequent endwise filament elongation occurring at only one actively growing end.

Example 4

Identification of Anionic Bodies as Nucleation Sites for Fibrillization

Anionic Surfaces are Sufficient for Induction of Tau Fibrillization. The endwise association of tau filaments with micelles and vesicles suggested that their interactions were stable. In the case of fusogenic proteins such as β-amyloid peptide, stable interactions are mediated by partial insertion of protein into the hydrophobic core of vesicles. It has been proposed that protein aggregation follows and is dependent upon this insertion. To determine whether tau fibrillization required hydrophobic insertion, tau was incubated in the presence of carboxylate-modified polystyrene microspheres. These bodies, which are available in a wide variety of carboxylate substitution densities, are impermeable to proteins. Anionic microsphere lots were chosen on the basis of molecular areas roughly corresponding to values observed for surfactant langmuir-blodgett monolayers. These vary from ~17–30 Å²/eq depending on the nature of the headgroup counterion. On the basis of measured aggregation numbers, however, micellar alkyl sulfate headgroup molecular areas may be as high as 60 Å²/eq. Therefore, microspheres with nominal molecular areas spanning the range 12–62 Å²/eq were employed for all experiments described below.

Figure 3:
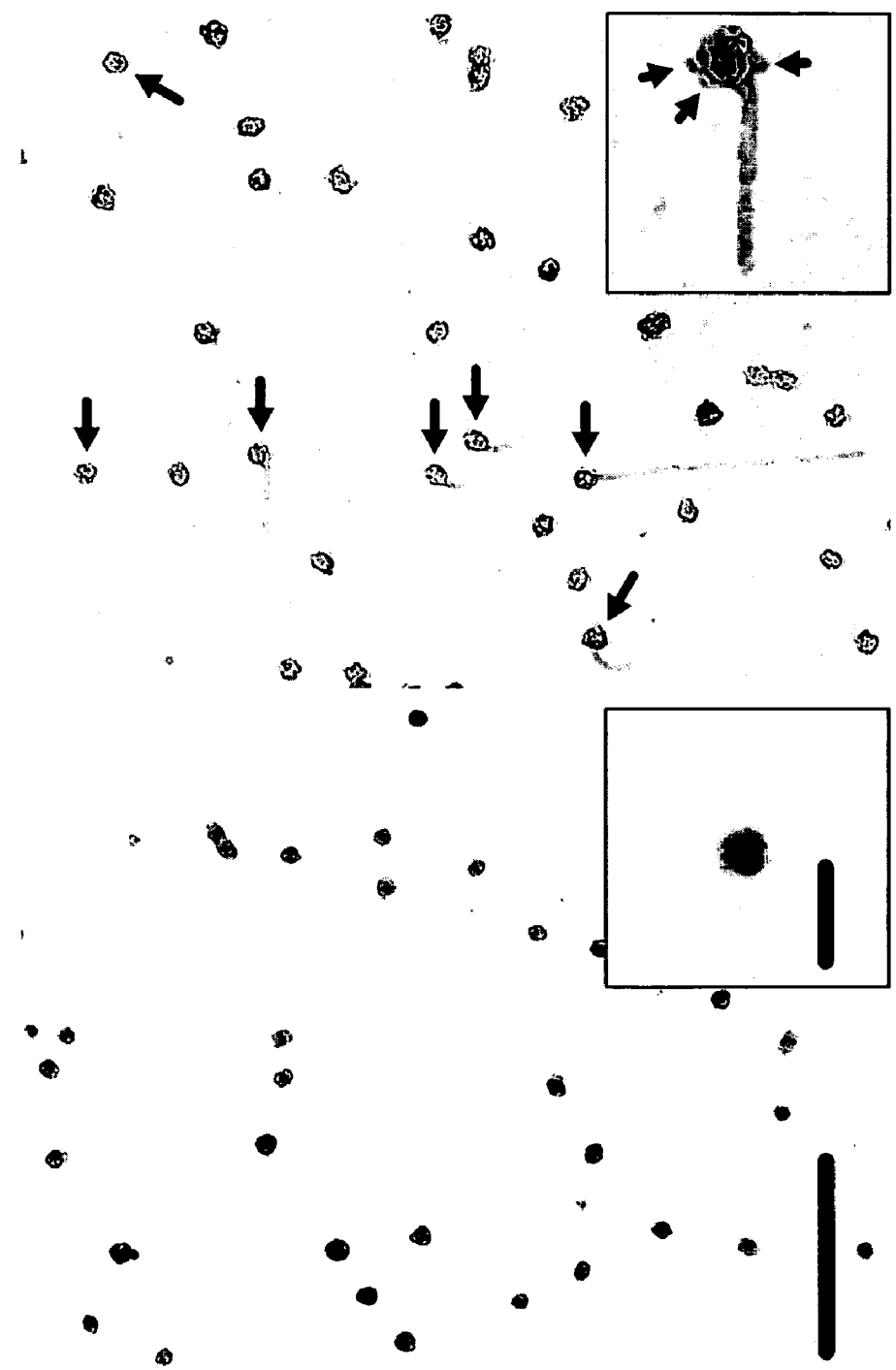
FIG. 3 shows Induction of tau Fibrillization Using Anionic Microspheres. Carboxylate-substituted polystyrene microspheres (90 nm diameter, 12 Å$^2$/eq molecular area; 591 pM) were incubated for 18 hours at 37° C. with Assembly Buffer in the A, absence or B, presence of htau40 (4 μM), then visualized by transmission electron microscopy. In the absence of protein, microspheres appeared as smooth-surfaced, roughly spherical objects without any associated filamentous material (A, inset). In contrast, incubation of microspheres in the presence of tau protein yielded rough surfaces that appeared enlarged relative to beads incubated in the absence of protein, with ~20% of microspheres having single filaments extending from their surfaces (arrows). Higher magnification (B, inset) revealed multiple short protrusions that may represent potential nucleation centers (arrowheads). Bar=500 nm; inset bar=100 nm.

In the absence of tau protein, microspheres (d=90 nm; molecular area=12 Å²/eq) incubated at 591 pM appeared in electron micrographs as spherical beads of roughly uniform dimension (FIG. 3A). After 18 h in the presence of tau, however, filaments with identical morphology as those induced by AA, anionic detergents, and anionic lipids could be seen extending from a subpopulation of microsphere surfaces, with nearly all filaments being microsphere associated (FIG. 3B). Closer inspection revealed that beads incubated in the presence of tau were larger than those incubated in its absence, and that much of the difference stemmed from densely staining material on the bead surface (FIG. 3B). Filaments appeared to grow out of this densely staining material. Although microspheres typically yielded only one mature filament per body, many had small (<10 nm) extensions on their surface with morphology similar to mature filaments (FIG. 3B, inset). These data suggest that simple adsorption onto impermeable anionic surfaces is sufficient to nucleate tau fibrillization, and that membrane penetration is not required.

Example 5

Microspheres as Fibrillization Inducer

Figure 4:
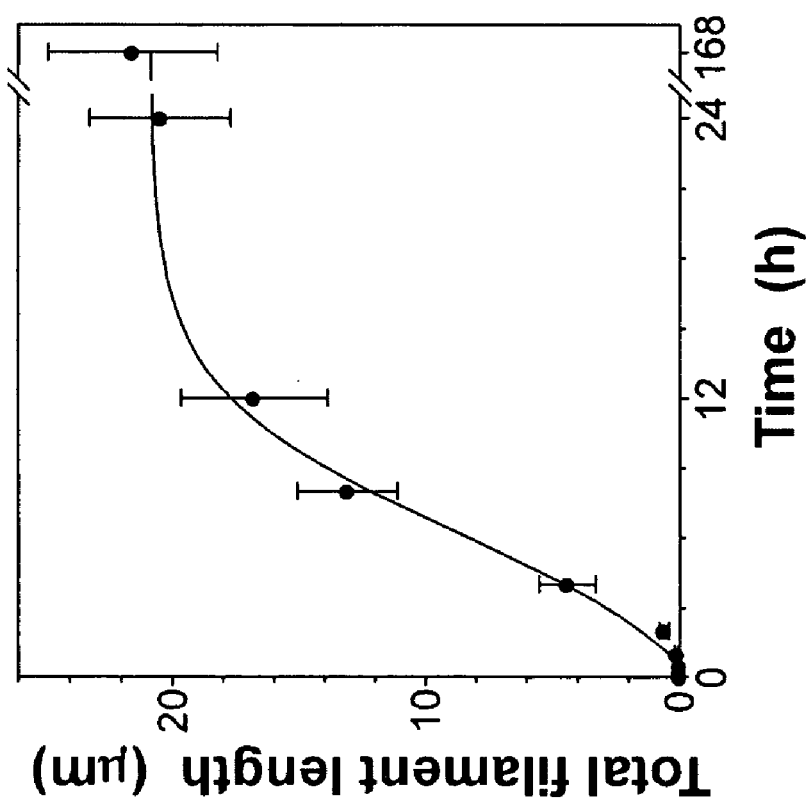
FIG. 4 shows a Time Course of Microsphere-mediated tau Fibrillization. Htau40 (4 μM) was incubated (37° C.) in Assembly Buffer in the presence of carboxylate-substituted polystyrene microspheres (90 nm diameter, 12 Å$^2$/eq molecular area; 124 pM) for 7 days, with aliquots removed and processed for transmission electron microscopy at the indicated time points. Each point represents the sum total length of all filaments >50 nm in length per field counted from 5–10 negatives at the indicated incubation time, whereas the solid line represents the best fit of all data points to a logistic regression (eq 2). Tau filament formation showed a clear lag phase, where no filaments were observed, followed by a phase of exponential increase, and ended in an equilibrium phase (achieved in ~24 h) after which further increases in filament length were not apparent.

Time Course of Microsphere-mediated tau Fibrillization. Because of their large uniform size and stability, microspheres offer the opportunity to visualize the nucleation and maturation of individual tau filaments. When the fibrillization of tau induced by 124 nM anionic microspheres (d=90 nm; molecular area=12 Å²/eq) was followed over 7 days by electron microscopy, total filament length was found to increase sigmoidally over time after a short period of absolute quiescence (FIG. 4), with equilibrium attained in ~24 h. Kinetic parameters of lag time and $k_{app}$ were derived from fitting these data to a logistic curve as described in Experimental Procedures (eq 2). Under these conditions, lag time was 3.1±0.5 h, $t_{50}$ was 7.1±0.4 h, and $k_{app}$ was 0.5±0.1 $h^{-1}$. Although no filamentous material >50 nm in length was detectable during the first 2 h of lag time (FIG. 4), accretion of the densely staining material on microsphere surfaces was apparent at the earliest time points (15 min). These data suggest that nucleation of tau fibrillization is a time-dependent process that occurs on the microsphere surface.

Example 6

Figure 5:
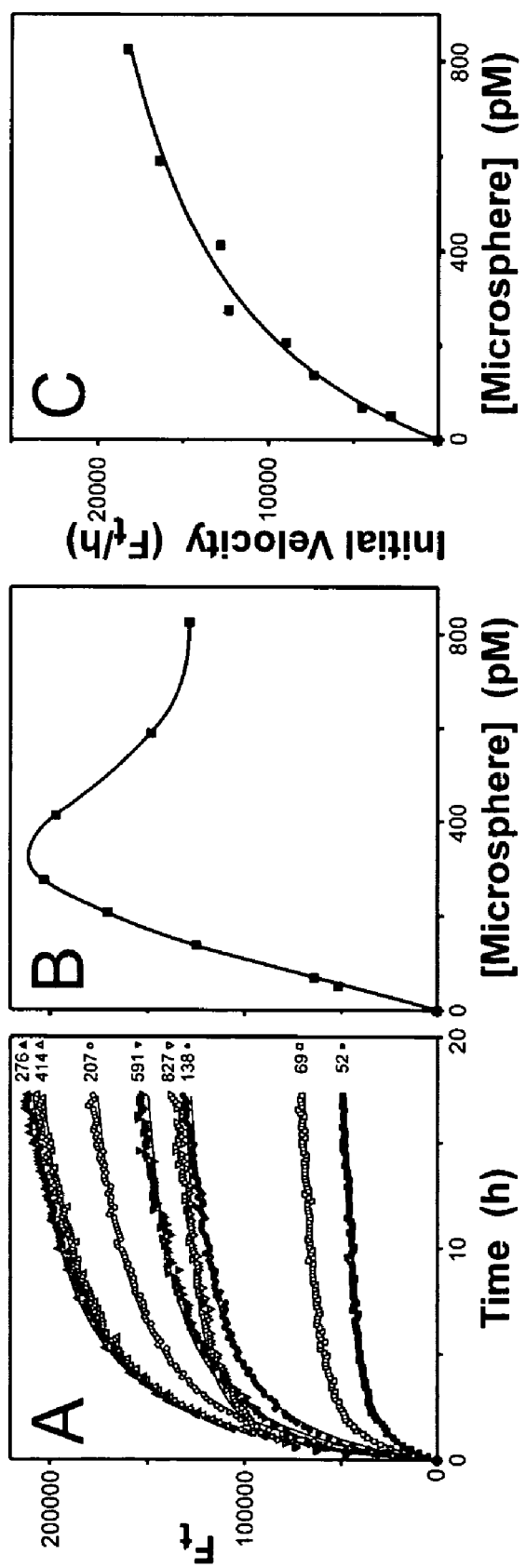
FIG. 5 shows a Time Course of Microsphere-mediated Increases in thioflavin S ("ThS") Fluorescence. Aggregation of htau40 (4 μM) in the presence of varying concentrations of carboxylate-substituted polystyrene microspheres (90 nm diameter, 12 Å$^2$/eq molecular area) was monitored using ThS (10 μM) fluorescence ($F_t$) as a function of time at 37° C. A, each point represents a fluorescence measurement, whereas each line represents the best nonlinear regression fit to a rectangular hyperbola (eq 3). Increasing concentrations of microspheres did not greatly change the half-time ($t_{50}$) of the reaction, which averaged 1.7±0.2 h when microspheres were ≦591 pM. B, replot of data in Panel A, where each point corresponds to the final equilibrium fluorescence level at a given microsphere concentration. The biphasic concentration dependence resembled surfactant aggregation inducers such as AA (20). C, replot of data in panel A, where each point represents the initial velocity of ThS fluorescence growth (F/h) at a given microsphere concentration (determined by fit of data in Panel A to eq 4), and the line represents the best fit to a rectangular hyperbola (eq 3). The initial rate of ThS fluorescence growth depended on microsphere concentration and appeared saturable.

Identification of a Tau Protein Intermediate in Anionic Body-Mediated Tau Fibrillization Tau Fibrillization Proceeds Through a ThS-positive Intermediate. The addition of AA to solutions of tau produces an immediate increase in particulate material, visible by electron microscopy, paralleled exactly by changes in the fluorescence of ThS, a non-covalent probe for beta sheet structure. Because measurable fibrils (i.e., filaments >50 nm in length) appear to grow from this particulate material, it has been suggested that the initial particulate material represents filament nuclei. However, the time course of fibrillization as determined by length measurements includes a distinct, isoform-dependent lag time, suggesting that the particulate material and ThS fluorescence observed at early time points actually reflects formation of an assembly competent intermediate. To clarify the temporal relationship between induction of ThS fluorescence and filament nucleation, the microsphere-induced tau aggregation time course described above was repeated in the presence of ThS. As with AA treatment, the addition of anionic microspheres induced an immediate increase in ThS fluorescence that continued hyperbolically over time (FIG. 5A). Fitting these curves as rectangular hyperbolas (eq 3) showed that most (except the highest microsphere concentration tested) shared similar $t_{50}$s, which averaged 1.7±0.2 h (n=7). These data show that the appearance of ThS fluorescence clearly precedes filament nucleation, with nearly two-thirds of equilibrium fluorescence levels attained by the end of fibrillization lag time, and with $t_{50}$ for maximal fluorescence occurring 5.4±0.7 h prior to the $t_{50}$ for fibrillization. Moreover, they suggest the existence of a prefibrillar, ThS-positive intermediate that appears early in the reaction pathway.

ThS Fluorescence Changes are Anionic-charge Dependent. Because of the stability of microspheres, it was possible to investigate the concentration dependence of ThS fluorescence change in greater detail than had been done previously with surfactant inducers such as AA. Like surfactant inducers, the dependence of induced ThS fluorescence on microsphere concentration (d=90 nm; molecular area=12 Å²/eq) was biphasic, with a clear optimum visible at ~375 pM (FIG. 5B). Well below this optimum, equilibrium fluorescence levels varied linearly with microsphere concentration. Yet despite the overall similarity in $t_{50}$ for most microsphere concentrations, the initial rate of fluorescence change varied significantly and depended directly on microsphere concentration (FIG. 5C). The concentration dependence of these initial rates fit a rectangular hyperbola (eq 3), with 50% maximum rate achieved at 370±50 pM microspheres. These data suggested that the interaction between tau protein and anionic surfaces directly influenced the initial rate of formation of the ThS-positive intermediate, and that the effect saturated at high microsphere:tau ratios.

Figure 6:
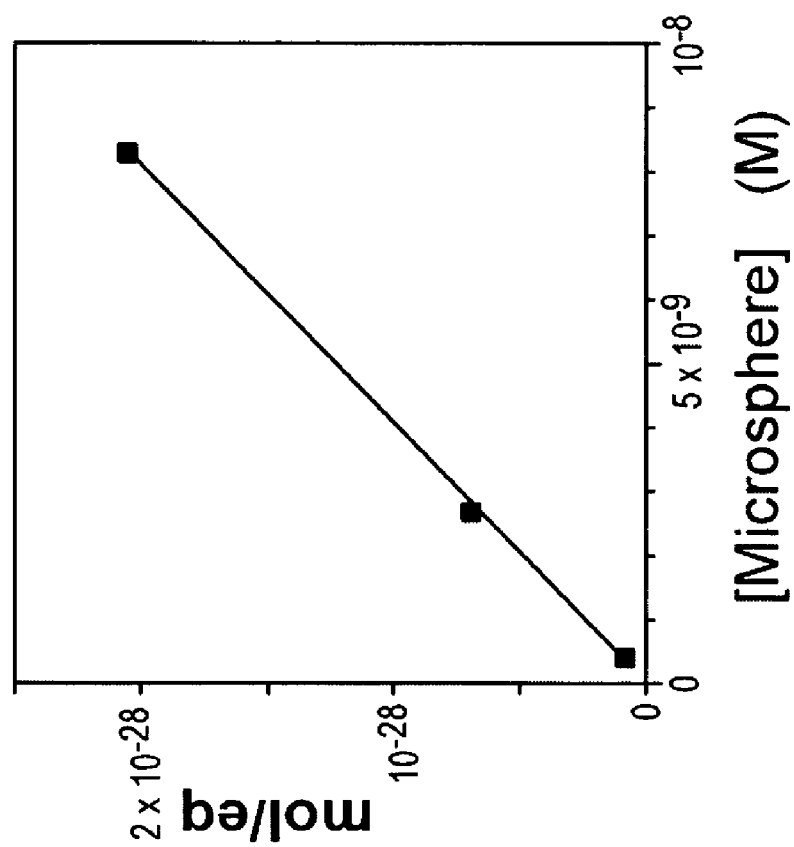
FIG. 6 provides data showing that Anionic Microsphere Potency is Directly Proportional to Surface Charge. Aggregation of htau40 (4 μM) in the presence of varying concentrations of three carboxylate-substituted polystyrene microsphere preparations that differed in size and surface charge density (diameter, molecular areas: 90 nm, 12 Å$^2$/eq; 60 nm, 46.7 Å$^2$/eq; and 40 nm, 62.0 Å$^2$/eq) was monitored using ThS (10 μM) fluorescence ($F_t$) as a function of time at 37° C. Although the dependence of $F_t$ on microsphere concentration was biphasic for each population, each microsphere population differed greatly in relative potency (data not shown). The figure shows a replot of this data, where each point represents the microsphere concentration yielding maximum $F_t$ against the inverse amount of negative charge (mol/eq; calculated from eq 5) of the three microsphere populations tested. The line represents linear regression analysis of the data points with slope equal to charge concentration (eq/1). Charge concentration, rather than molecular area or microsphere size, is the principal determinant of potency with respect to ThS fluorescence.

To determine the influence of charge density on intermediate formation, the time course and concentration dependence of three microsphere preparations (diameter, molecular areas: 90 nm, 12 Å$^2$/eq; 60 nm, 47 Å$^2$/eq; 40 nm, 62 Å$^2$/eq) was investigated. All three preparations induced ThS fluorescence with biphasic concentration dependence, but with very different initial rates and optimal concentrations. Plots of optimal molar concentration of microspheres against their amount of surface charge were linear with slope equal to concentration of charge (FIG. 6). Dependence of initial rates on charge concentration was linear as well (data not shown). These results suggest that the principal function of anionic surfaces early in the assembly pathway is to promote the formation of a ThS-positive, assembly competent intermediate, and that their potency in this regard is directly dependent on their anionic charge density.

Figure 7:
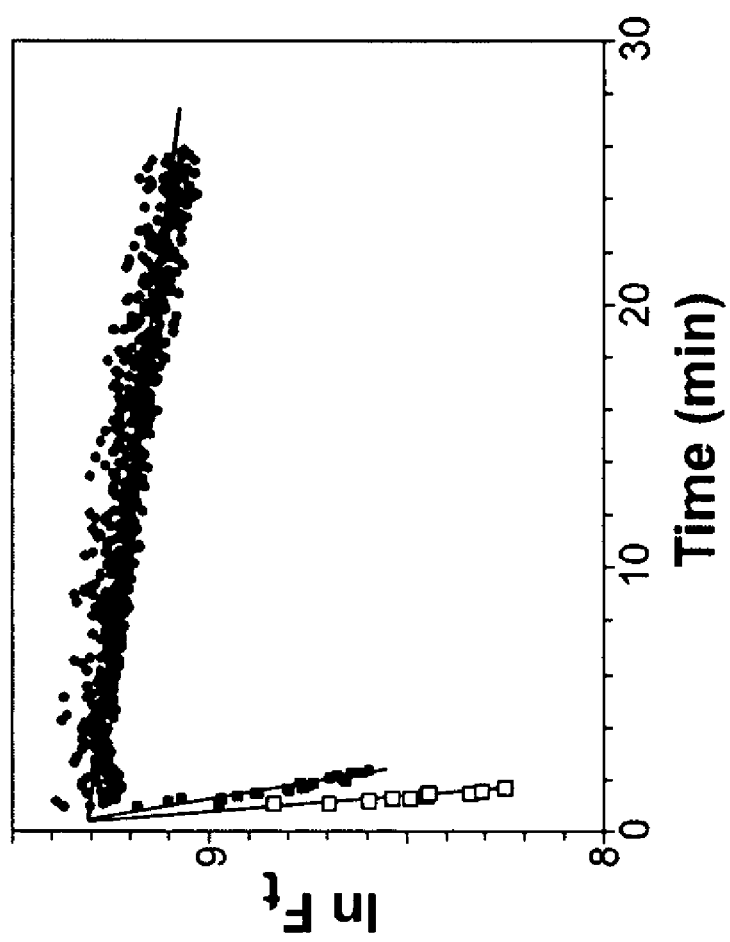
FIG. 7 shows Disaggregation of Synthetic tau Filaments. Htau40 (4 μM) aggregated in the presence of Assembly Buffer containing AA (75 μM) and ThS (2 μM) for 3 h at room temperature was diluted 20-fold into Assembly Buffer containing ThS (2 μM) and either 4 μM htau40 (■), 50 μM arachidonic acid (●), or no additions (□). Each point represents ThS fluorescence ($F_t$) measured as a function of time after dilution, and the line is the best fit of the data points to a first order decay. Stability of the ThS signal depended on the presence of AA.

The ThS-positive Intermediate is Metastable. The stability of the ThS intermediate formed by aggregating htau40 for 3 h at room temperature was examined. Under these conditions, most of the ThS fluorescence resulted from interaction with the intermediate. Rapid, 20-fold dilution of the sample into Assembly Buffer alone with stirring dropped AA concentrations below the CMC and led to loss of ThS fluorescence with an first order rate of 49.8 h$^{-1}$ (FIG. 7) Dilution into Assembly Buffer containing 2 μM htau40 (i.e., above the minimal concentration needed to support fibrillization) slowed the decay rate only modestly to 23.4 h$^{-1}$. In contrast, dilution into buffer containing 50 μM arachidonic acid (i.e., above the CMC) yielded a decay rate to 0.5 h$^{-1}$; 50-fold slower than dilution in buffer alone. These data show that ThS fluorescence is readily reversible and dependent on the presence of micelles for stability. For purposes of comparison, filament stability also was quantified using the electron microscopy assay. When diluted 20-fold into Assembly Buffer alone, total filament length did not change significantly (p<0.05) over 90 min of incubation. Thus the intermediate detected by ThS is far less stable than filamentous tau, and therefore is probably not fibrillar.

Figure 8:
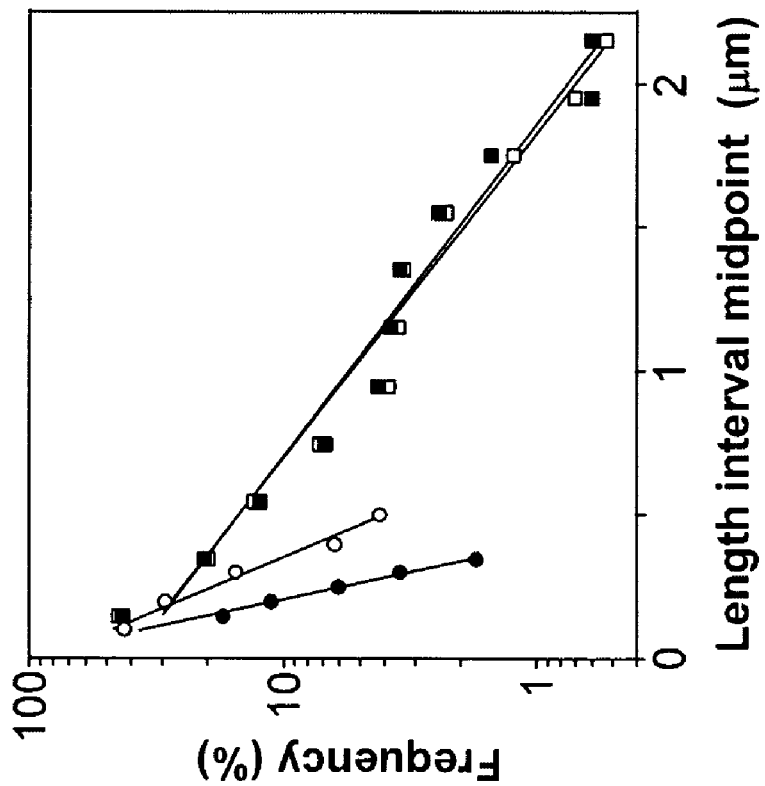
FIG. 8 shows Microsphere-induced tau Fibrillization Yields Exponential Length Distributions. Htau40 (4 μM) was incubated (6 h at 37° C.) in the presence of 124 pM carboxylate-substituted polystyrene microspheres (90 nm diameter, 12 Å$^2$/eq molecular area), and then examined by transmission electron microscopy at 8,000-fold magnification. The lengths of all filaments (□)≧50 nm in length and also the filament subpopulation associated end-wise with microspheres (■) were then measured from digitized images and plotted. Each data point represents the percentage of analyzed filaments (n=664 and 575 for total and microsphere-associated populations, respectively) that segregated into consecutive length intervals (200-nm bins), whereas each line represents the best fit of data points to an exponential regression (eq 6). Under these conditions, 86.6±2.8% of all measurable synthetic filaments were microsphere associated, with nearly identical percentages seen in individual bins. For comparison, the length distributions (50 nm bin size) of authentic, AD-brain derived tau filaments were calculated from the literature (FIG. 1A of Ref. 46; n=95; ●) and from freshly analyzed material (n=140; ○) prepared as in (19). Although their average lengths differ, both authentic tau filament preparations adopt an exponential length distribution.

Origin of Exponential Length Distributions. In vitro fibrillization of tau with surfactants invariably produces exponential distributions of filament lengths. These may result from shear-dependent breakage during preparation, time dependent nucleation, or from energy distributions at equilibrium. To clarify this issue, the length distributions of filaments formed during incubation with anionic microspheres was calculated and plotted on a semilogarithmic scale. After 6 h of incubation, filament distributions were nearly exponential, with most filaments (86.6±2.8%) being microsphere associated through one end (FIG. 8). In contrast, only 13.6%±1.8% (n=1314 observations) of microspheres had nucleated filaments >50 nm in length. The absence of significant numbers of isolated filaments rules out shearing as an influence on length distribution. Moreover, as shown previously with dithiothreitol as inducer, length distributions were exponential at the earliest measurable time points (4 h; data not shown), suggesting that equilibrium considerations also were not a factor. Rather, the data suggest that length distributions reflect the kinetic mechanism of assembly, and arise from the exponential increase in filament length as a function of time.

For purposes of comparison, length distributions of authentic filaments purified from AD brain by two differential centrifugation-based methods also were calculated. Both preparations adopted near exponential length distributions, with slope constants (b; calculated from eq 6) of −5.3±0.2 and −2.7±0.2 μm$^{-1}$ (FIG. 8). These closely paralleled values for synthetic filaments aggregated 3 h with AA (b=−5.4±0.2 μm$^{-1}$; FIG. 1 in Ref. 12) but were much shorter than those formed from microspheres (FIG. 8; b=−0.88±0.07 μm$^{-1}$), presumably because the latter formed fewer nucleation centers over a longer period of time. Although purified filaments correspond to only a fraction of filamentous material in brain, their length distributions are consistent with time dependent processes such as those described here underlying filament formation in disease.

Example 7

Determination of Fibrillization Kinetics

Fibrillization follows classic nucleation-dependent kinetics, consisting of a nucleation phase characterized by a pronounced lag time, followed by an exponential growth phase characterized by an apparent first order growth rate, $k_{app}$, and then an equilibrium phase where further filament growth ceased. Typically, only one filament >50 nm in length matures per microsphere, although morphological evidence suggested that multiple nucleation events are possible. Assuming similar behavior for anionic surfactant micelles explains the differing length distributions and concentration dependencies measured for htau40 and AA, $C_{18}H_{37}NaSO_4$, and $C_{20}H_{41}NaSO_4$. The number of filaments reflects the number of nucleation centers, which is proportional to the micelle concentration and thus dependent on the interplay between CMC and aggregation number:

$$m=(S_T-CMC)/N_a \qquad (7)$$

where m is micelle concentration, $S_T$ is total surfactant concentration, and $N_a$ is the aggregation number. Up to the peak of its biphasic dose response curve, increasing micelle concentrations yield more nucleation centers and therefore more filaments that, at constant tau concentration, achieve shorter average lengths. Comparison among tau isoforms is more complicated, as these differ in the concentration dependence of nucleation as reflected in lag time.

Once nucleated, tau filaments grow unidirectionally from the inducer surface. The presence of only one actively growing end distinguishes the pathway described here from spontaneous aggregation pathways followed by other amyloids. At equilibrium, tau filaments remain associated with nucleation centers, explaining the substoichiometric recovery of AA with filaments. Previously, this observation was ascribed to transient association, but the work presented herein suggests it derives from unidirectional elongation combined with stable association. The final length distribution of the filament population is exponential owing to the time dependent nucleation event, as opposed to filament breakage or equilibrium considerations. Authentic, AD-derived filaments also show exponential length distributions, suggesting that time-dependent nucleation events such as those described here may play a role in their formation. However, purified filaments represent only a portion of total filaments in AD lesions, and also the susceptibility of isolated filaments to shearing and breakage has been noted previously. Thus, estimates of the length distribution and number average length of authentic filaments must be interpreted with caution.

Example 8

Assays for α-Synuclein Fibrillization

α-synuclein Expression and Purification. α-synuclein (Registry number 480802–48–0) was amplified by PCR from a human brain cDNA library (Stratagene, La Jolla, Calif.) using the following primers containing NdeI and HindIII restriction sites. The PCR product was cloned directly into PCR-BluntII-TOPO vector (Invitrogen, Carlsbad, Calif.). The construct was subjected to restriction digest with NdeI and HindIII, and the resultant α-synuclein insert was ligated into the pT7c vector. His-tagged α-synuclein protein was expressed and purified as described previously for tau protein.

α-synuclein Polymerization Assays. Under standard conditions, α-synuclein (4–70 μM) was incubated with AA or other polymerization inducers (25–3000 μM) in Assembly Buffer (10 mM HEPES, pH 7.4, 100 mM NaCl, 5 mM DTT) at 37° C. for 3–26 h, without agitation. Various inducer concentrations were prepared by serial dilution of stock solutions. Control reactions were normalized for 1:1 $H_2O$ isopropanol vehicle, which was limited to 5% in all reactions. Samples were processed for electron microscopy and fluorescence spectroscopy as described below.

Thioflavin T assay. α-synuclein (4–70 μM) was incubated in Assembly Buffer in the presence of 20 μM thioflavin T, with or without assembly inducers, in 96-well plates. Aggregation was monitored by following thioflavin T fluorescence ($\lambda_{ex}$=385 nm and $\lambda_{em}$=440 nm; in a Flex Station plate reader (Molecular Devices, Sunnyvale, Calif.).

Nomenclature. Polyoxyethylene detergents of formula $CH_3(CH_2)_y$—$O(CH_2CH_2)_x$—H are referred to as $C_{(y+1)}E_x$, where y and x are the number of methylene and oxyethylene groups, respectively. Sodium alkyl sulfate and alkyl tetramethyl ammonium bromide detergents are referred to by their chemical formulas.

Figure 9:
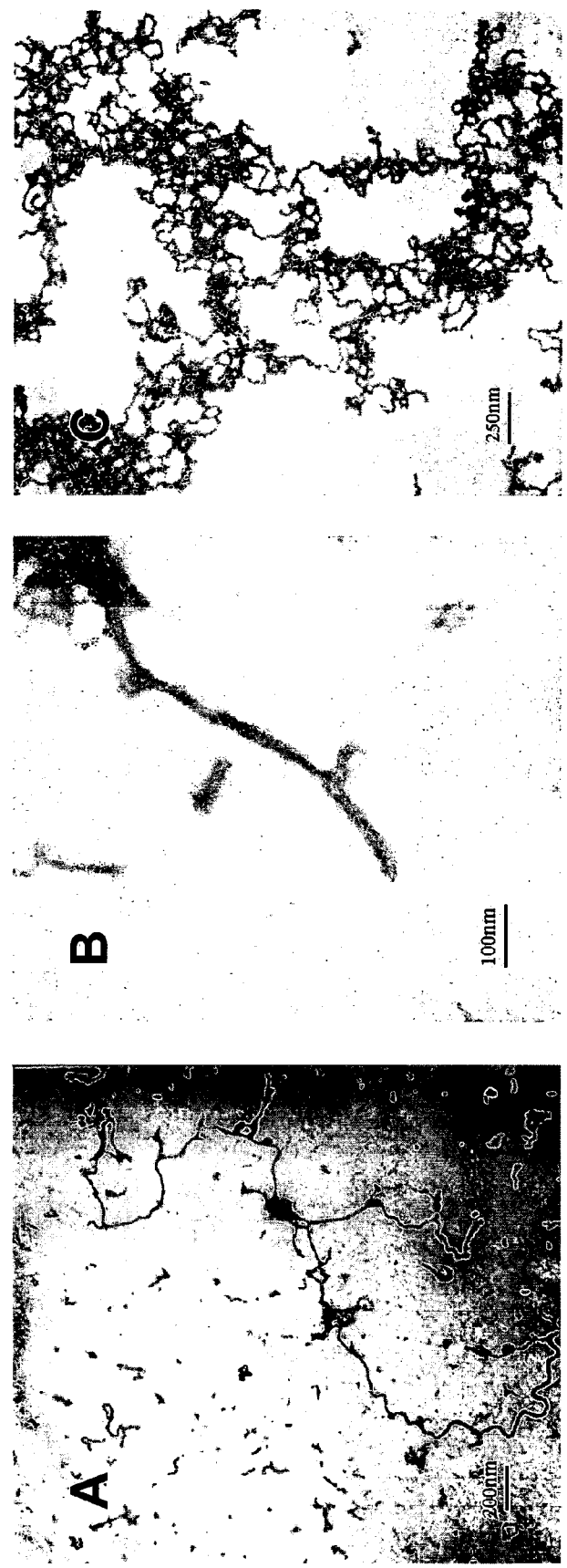
FIG. 9 shows AA and Alkyl Sulfate Detergents Induce α-synuclein Fibrillization. α-synuclein (A, 4 μM; B, 70 μM; or C, 30 μM) was incubated (A, B, 4 h; C, 16 h) at 37° C. without stirring in the presence of A, 200 μM AA; B, 1000 μM AA; or C, 100 μM $C_{14}H_{29}NaSO_4$ and then examined by electron microscopy at 35,000-, 100,000-, and 45,000-fold magnification, respectively. Both straight and twisted fibril morphologies are apparent.

Electron Microscopy. Aliquots of polymerization reactions were taken, treated with 2% glutaraldehyde (final concentration), mounted on formvar/carbon coated 300 mesh grids, and negatively stained with 2% uranyl acetate as described previously (King et al., 1999). Images were viewed in a Phillips CM 12 transmission electron microscope operated at 65 kV. Random images were captured on film at 8,000–22,000X magnification, digitized at 600 dots-per-inch resolution, and imported into Optimas 6.5.1 for quantification of filament lengths and numbers. Individual filaments were defined as any object greater than 50 nm in its long axis and were counted manually.

α-synuclein influence on CMC and induction of fibrillization. The utility of these findings were extended to α-synuclein. α-synuclein fibrillization was induced by AA and anionic detergents (but not nonionic or cationic detergents) at 37° C. (FIG. 9). Fibrils were obtained at α-synuclein concentrations ranging from 4 to 70 μM and had both straight and twisted morphology with widths varying from 5 to 14 nm for the straight filaments (typically 10 nm), and from 12 to 20 nm for twisted fibrils (FIG. 9). These data suggest that synthetic α-synuclein filaments formed from anionic detergents and fatty acids were morphologically similar to those obtained from recombinant α-synuclein without inducer and to those found in disease.

As with tau protein, incubation of α-synuclein with anionic detergents and AA led to a large depression of CMC (Data not shown), again suggesting that these inducers were mostly micellar at active concentrations. Filament yield was quantified as a function of inducer and α-synuclein concentration using the Thioflavin T assay. As with tau protein, all dose response curves for anionic detergents and AA were biphasic, with maximal filament yield dependent on α-synuclein concentration. Representative data from the Thioflavin T assay is shown for the anionic detergent $C_{12}H_{25}SO_4Na$ in FIG. 11. In this example, induction of α-synuclein fibrillization required a threshold of approximately 100 μM $C_{12}H_{25}SO_4Na$, above which Thioflavin T fluorescence increased biphasically with maximal fluorescence dependent on α-synuclein concentration. The threshold for induction activity corresponded to the CMC for $C_{12}H_{25}SO_4Na$ a, confirming the importance of micellization for inducer activity.

Figure 11:
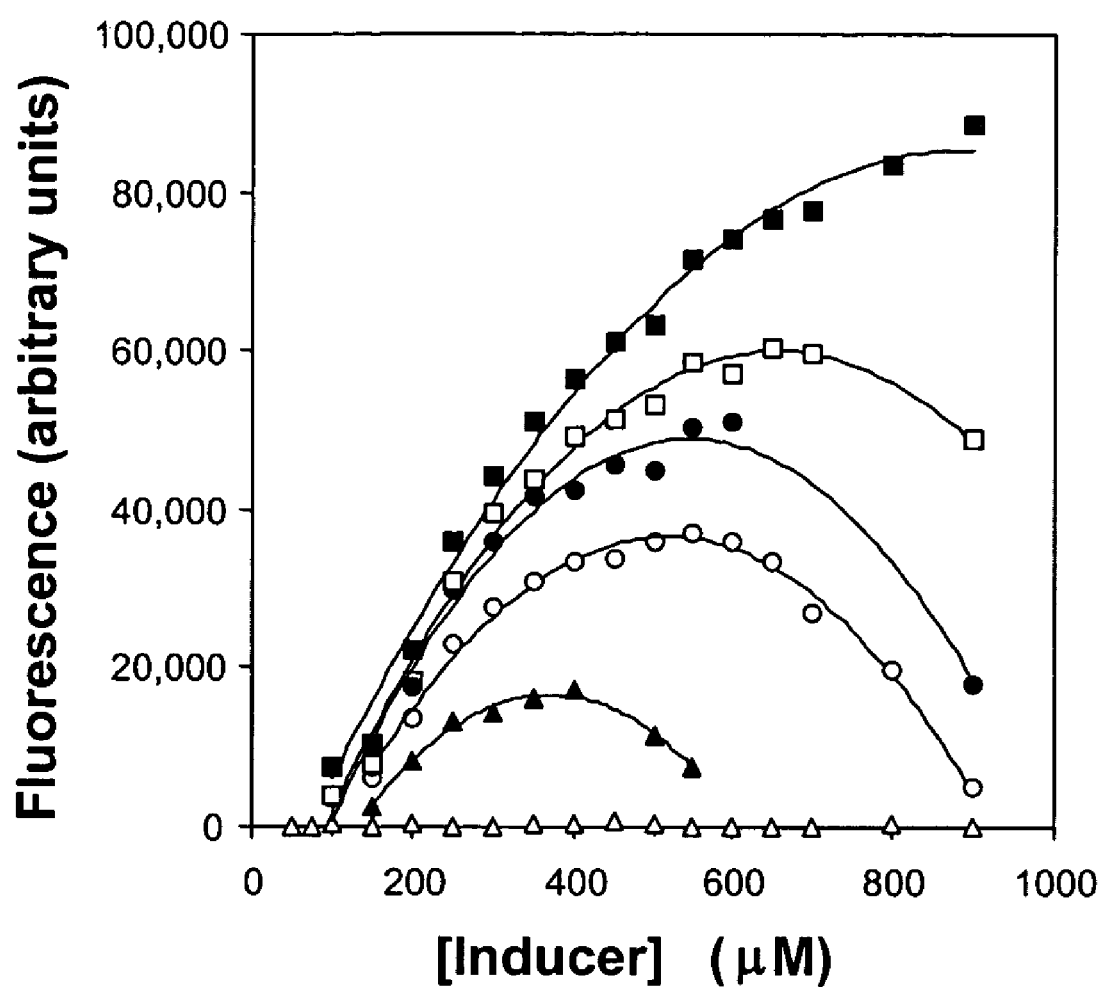
FIG. 11 shows α-synuclein fibrillization as a function of protein and inducer concentrations. α-synuclein (5 μM (▲); 10 μM (○); 15 μM (●); 20 μM (□); or 30 μM (■, △) was incubated (16 h at 37° C.) in the presence of varying concentrations of $C_{12}H_{25}SO_4Na$ (▲, ○, ●, □, ■) or heparin (△) and the resultant fibrillization assayed using Thioflavin T fluorescence. Each point represents Thioflavin T fluorescence corrected using inducer-only and α-synuclein-only control reactions. Each line represents the best polynomial fit to each set of data points. Induction of α-synuclein fibrillization required a threshold of approximately 100 μM $C_{12}H_{25}SO_4Na$, above which Thioflavin T fluorescence increased biphasically with maximal fluorescence dependent on α-synuclein concentration. In contrast, heparin treatment (shown in units of μM sacharide monomer) induced α-synuclein fibrillization only weakly.

For purposes of comparison, a broad range of Heparin (both sodium salt Grade I-A and heparin sodium salt) concentrations (25–3000 μM saccharide monomer) were tested for their ability to induce α-synuclein fibrillization. Electron microscopy showed little measurable polymerization. Although few hundred counts (<600) could be measured by Thioflavin T assay for both forms of heparin, similar to a previous report, the signal was small relative to the one obtained for the detergent and AA induced α-synuclein assembly (FIG. 11). This suggests that both straight alkyl chain anionic detergents and AA produce more filamentous α-synuclein than heparin. Also, heparin-induced polymerization in the presence of continuous shaking, described previously, required α-synuclein concentrations grater than 3 μM. In contrast, anionic detergent-mediated fibrillization was obtained at 41 μM α-synuclein (Data not shown).

Figure 12:
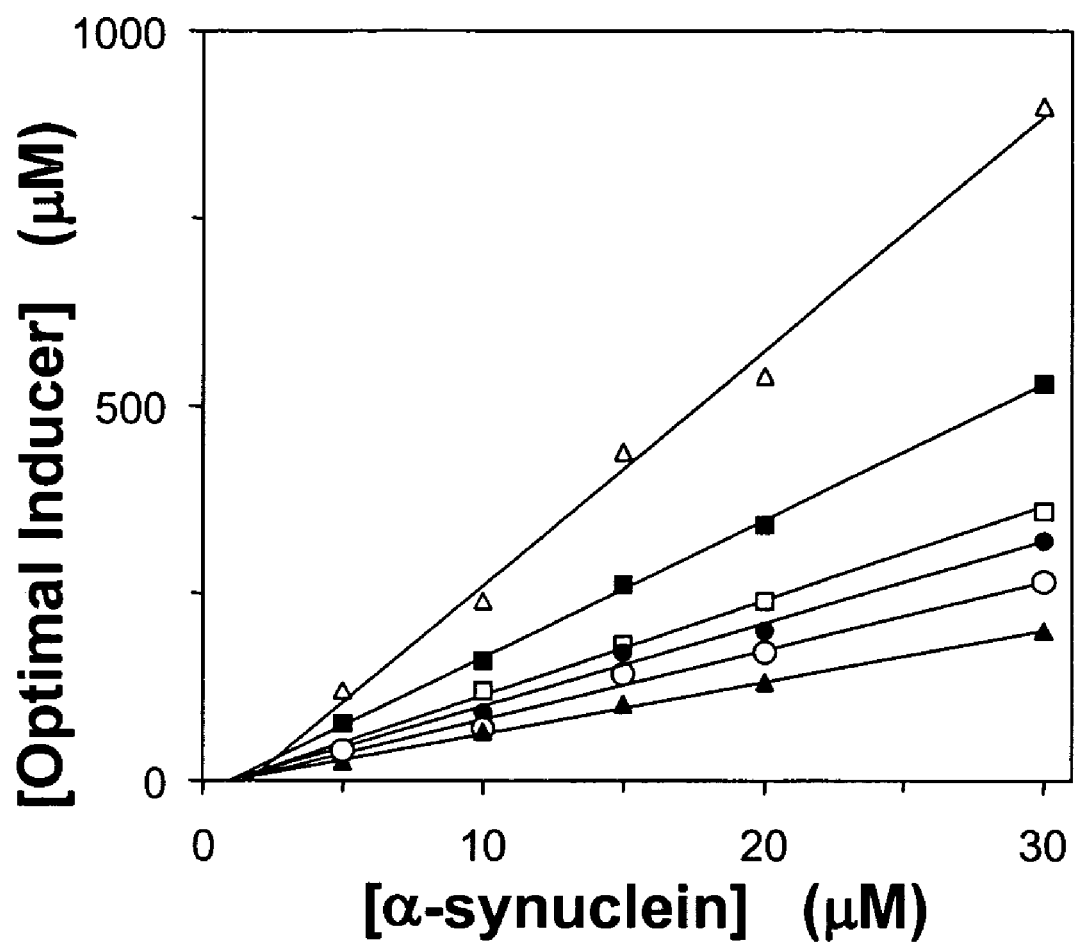
FIG. 12 shows Anionic Detergents and AA lower the critical concentration for α-synuclein fibrillization. The concentration of $C_{20}H_{41}SO_4Na$ (▲), $C_{18}H_{37}SO_4Na$ (○), $C_{17}H_{35}SO_4Na$ (●), $C_{16}H_{33}SO_4Na$ (□), $C_{14}H_{29}SO_4Na$ (■), and arachidonic acid (△) required for maximum Thioflavin T fluorescence was determined from dose response data (see FIG. 1) and plotted against α-synuclein concentration. Each line represents linear regression analysis of the data points for each inducer. The x-axis intercept corresponds to the critical concentration for α-synuclein fibrillization. This value varied from 0.9–2 μM for the alkyl sulfate detergents and arachidonic acid.

Anionic detergents induced α-synuclein assembly proceeds at low concentrations of α-synuclein. When detergent concentrations that yielded maximum polymerization (obtained from Thioflavin T assay; FIG. 11) were potted against α-synuclein concentration, a linear fit was obtained (FIG. 12). The x-axis intercept was between 0.9 and 2 μM α-synuclein for all detergents examined (Table I). Thus the minimum α-synuclein concentration required for measurable detergent-induced fibrillization under optimal conditions is low micromolar. This value is far below the critical concentration of 27–200 μM α-synuclein found in prior art.

Figure 10:
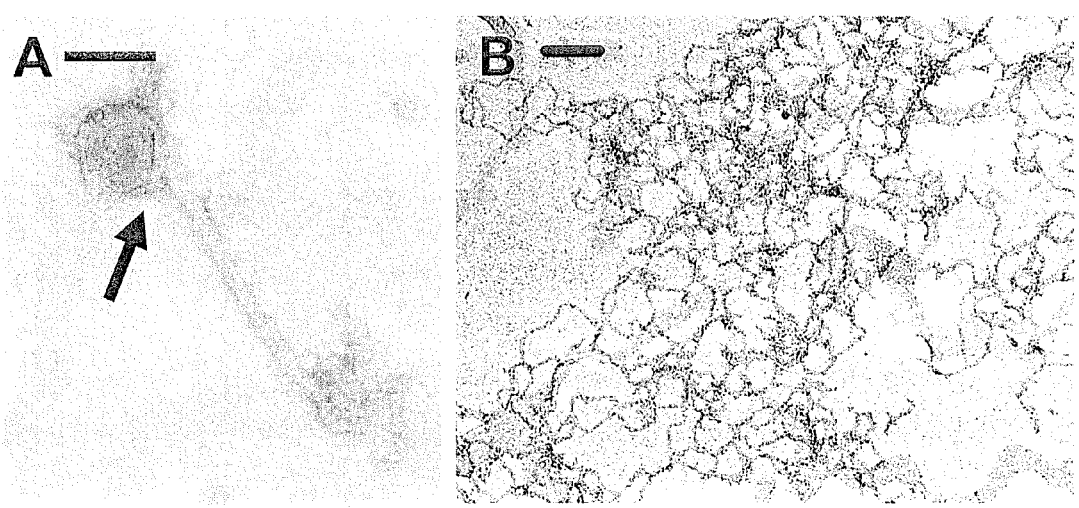
FIG. 10 shows Stimulation of α-synuclein Fibrillization by Anionic Lipid. α-synuclein (A, 5 μM; B, 50 μM) was incubated (4 h at 37° C.) with performed phosphatidic acid (A, 200 μM) or phosphatidylserine (B, 100 μM) vesicles and then examined by transmission electron microscopy (22,000-fold magnification). Both lipids induced α-synuclein fibrillization. Vesicles associated with at least one filament end was a common observation for all the samples incubated in the presence of phosphatidic acid (arrow). Bars=100 nm.

Phosphatidylserine (PS) and phosphatidic acid (PA) anionic liposomes induce α-synuclein fibrillization. To determine whether anionic lipids could substitute for anionic detergents or free fatty acids as polymerization inducers 5, 10, 25, and 50 μM α-synuclein reactions were incubated under standard polymerization conditions for four hours at 37° C. in the presence of freshly prepared liposomes. Lipid concentrations ranged between 25 and 400 μM. Abundant filaments and/or filamentous conglomerates were observed with phosphatidylserine under all conditions (FIG. 10). Phosphatidic acid was second in potency and induced the formation of significant amounts of filamentous material under all conditions tested (FIG. 10). The zwitterionic lipid phosphatidylcholine was the least efficient inducer and gave rise to only to modest quantities of polymer. Unlike detergent micelles, the phospholipid vesicles are readily observable in electron microscopy assays owing to their large size (typically >100 nm radius compared to <10 nm radius for detergents). Vesicle associated filaments at one or both ends were a common observation in both the phosphatidic acid and the phosphatidylserine induced polymerization reactions (FIG. 10). These data support the hypothesis that anionic surfaces presented by detergents or free fatty acids in micellar form or by lipids in vesicular form are capable of inducing α-synuclein filament formation, and suggest that at least part of the mechanism of polymerization induction may involve nucleation of filaments at the micelle/vesicle surface in a paradigm similar to the one we previously described above for recombinant tau protein.

What is claimed is:

1. A screening method for identifying inhibitors of protein filament formation, comprising:

a) providing:

i) a protein monomer associated with formation of intra- or extra-cellular aggregates;
ii) a fibrillization inducer selected from the group consisting of anionic microparticles, anionic support surfaces, and anionic surfactants having an alkyl chain comprising at least 12 carbon atoms and a non-carboxylate anionic head group; and
iii) a test compound;
b) combining said protein monomer and said fibrillization inducer in one or more control reaction vessels;
c) combining said protein monomer, said fibrillization inducer, and said test compound in one or more test reaction vessels; and
d) analyzing the contents of the control reaction vessels of step (b) and the test reaction vessels of step (c) for the formation of proteinaceous polymeric filaments,
wherein absence or a reduction in the size or stability of proteinaceous polymeric filaments in the test reaction vessels of step (c) as compared to proteinaceous polymeric filaments in the control reaction vessels of step (b) indicates that the test compound is an inhibitor of proteinaceous polymeric filament formation.

2. The method of claim 1 wherein the monomer selected from the group consisting of tau monomer and u-synuclein monomer and is provided at a concentration from 1 to 70 μM.

3. The method of claim 2 wherein the monomer is provided at a concentration of 4 μM.

4. The method of claim 1 wherein the fibrillization inducer is an anionic surfactant provided at a concentration from 50 to 150 μM.

5. The method of claim 4 wherein the fibrillization inducer is an anionic surfactant selected from the group consisting of sulfate detergents, sulfonate detergents, and phosphate detergents.

6. The method of claim 4 wherein the an anionic surfactant is selected from the group consisting of alkyl sulfate detergents, alkyl polyol sulfate detergents, alkyl thiosulfate detergents, alkyl oxypropyl sulfate detergents, alkyl oxyethylene sulfate detergents, alkyl sulfonate detergents, hydroxy alkyl sulfonate detergents, alkaryl sulfonate detergents, and para alkaryl sulfonate detergents.

7. The method of claim 4 wherein the anionic surfactant has an alkyl chain that is either saturated or unsaturated.

8. The method of claim 4 wherein the anionic surfactant is an anionic phospholipid.

9. The method of claim 8 wherein the anionic phospholipid is selected from the group consisting of phosphatidylserine and phosphatidic acid.

10. The method of claim 1 wherein the monomer is a tau monomer and the fibrillization inducer is an anionic surfactant having the chemical formula $C_{18}H_{37}SO_4Na$.

11. The method of claim 1 wherein the monomer is α-synuclein and the fibrillization inducer is an anionic surfactant having the chemical formula $C_{12}H_{25}SO_4Na$.

12. The method of claim 1 wherein the fibrillization inducer is an anionic microsphere having a molecular area from 12–62 Å$^2$/eq.

13. The method of claim 1 wherein the fibrillization inducer is an anionic microsphere having a diameter ranging from 30–1000 nm.

14. The method of claim 1 wherein said monomer, said fibrillization inducer, and said test compound combined in step (c) are combined either simultaneously or sequentially.

15. The method of claim 14 wherein said monomer and said fibrillization inducer of step (c) are combined first, then said test compound is added to the combination.

16. The method of claim 14 wherein said monomer and said test compound of step (c) are combined first, then said fibrillization inducer is added to the combination.

17. The method of claim 14 wherein said fibrillization inducer and said test compound of step (c) are combined first, then said monomer is added to the combination.

18. The method of claim 1 wherein the method of analysis of the contents of the control and test reaction vessels is selected from the group consisting of electron microscopy, fluorescence spectroscopy, ultracentrifugation, and light scattering.

19. A model system for identifying inhibitors of tau protein fibrillization, comprising tau monomer and a fibrillization inducer selected from the group consisting of anionic microparticles, anionic support surfaces, and micellar anionic surfactants having an alkyl chain comprising at least 12 carbon atoms and a non-carboxylate anionic head group, wherein the tau monomer and the fibrillization inducer interact to induce the formation of tau filaments.

20. A model system for identifying inhibitors of α-synuclein protein fibrillization, comprising α-synuclein monomer and a fibrillization inducer selected from the group consisting of anionic microparticles, anionic support surfaces, and micellar anionic surfactants having an alkyl chain comprising at least 12 carbon atoms and a non-carboxylate anionic head group, wherein the α-synuclein monomer and the fibrillization inducer interact to induce the formation of α-synuclein filaments.

21. A method for identifying drugs useful in the treatment of Alzheimer's Disease, comprising: contacting tau protein monomer with a tau fibrillization inducer selected from the group consisting of anionic microparticles, anionic support surfaces, and anionic surfactants having an alkyl chain comprising at least 12 carbon atoms and a non-carboxylate anionic head group, and a test compound, and determining whether the test compound inhibits tau fibrillization.

22. The method of claim 1 wherein the tau protein monomer is a tau protein monomer provided at a concentration of 1 to 70 μM, and wherein the fibrillization inducer is an anionic surfactant provided at a concentration from 50 to 150 μM, and is selected from the group consisting of sulfate, detergents, sulfonate detergents, and phosphate detergents.

23. The method of claim 22 wherein the tau protein monomer is provided at a concentration of 4 μM, and wherein the tau fibrillization inducer has the chemical formula $C_{18}H_{37}SO_4Na$.

24. A method for identifying drugs useful in the treatment of Parkinson's Disease, comprising: contacting an α-synuclein monomer with an α-synuclein fibrillization inducer selected from the group consisting of anionic microparticles, anionic support surfaces, and anionic surfactants having an alkyl chain comprising at least 12 carbon atoms and a non-carboxylate anionic head group, and a test compound, and determining whether the test compound inhibits α-synuclein fibrillization.

25. The method of claim 24 wherein the α-synuclein monomer is provided at a concentration of 1 to 70 μM, and wherein the α-synuclein fibrillization inducer is an anionic surfactant provided at a concentration from 50 to 150 μM, and is selected from the group consisting of sulfate, carboxylate detergents, sulfonate detergents, and phosphate detergents.

26. The method of claim 25 wherein the α-synuclein protein monomer is provided at a concentration of 4 μM, and wherein the α-synuclein fibrillization inducer has the chemical formula $C_{12}H_{25}SO_4Na$.

27. A method for identifying inhibitors of protein fibrillization which are specific for intermediates of fibrillization comprising the steps of the method of claim 1, wherein the protein monomer is provided at a concentration from 0.1 to 5 µM.

28. A method for identifying inhibitors of protein fibrillization which specifically inhibit filament nucleation, elongation or stability comprising the steps of the method of claim 1, wherein the protein monomer is provided at a concentration from 2 to 5 µM.

* * * * *